US011786697B2

(12) United States Patent
Christian et al.

(10) Patent No.: US 11,786,697 B2
(45) Date of Patent: Oct. 17, 2023

(54) ACCESS PORT AND CATHETER ASSEMBLY INCLUDING CATHETER DISTAL PORTION STABILITY FEATURES

(71) Applicant: C. R. Bard, Inc., Franklin Lakes, NJ (US)

(72) Inventors: Kelly J. Christian, Draper, UT (US); Daniel B. Blanchard, Bountiful, UT (US); Ryan C. Patterson, Farmington, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 310 days.

(21) Appl. No.: 17/161,414

(22) Filed: Jan. 28, 2021

(65) Prior Publication Data

US 2021/0146094 A1    May 20, 2021

Related U.S. Application Data

(63) Continuation of application No. 16/362,531, filed on Mar. 22, 2019, now Pat. No. 10,905,850, which is a
(Continued)

(51) Int. Cl.
*A61M 25/00* (2006.01)

(52) U.S. Cl.
CPC ...... *A61M 25/0043* (2013.01); *A61M 25/003* (2013.01); *A61M 25/008* (2013.01);
(Continued)

(58) Field of Classification Search
CPC .. A61M 2025/0024; A61M 2025/0031; A61M 2025/0035; A61M 2025/0037;
(Continued)

(56) References Cited

U.S. PATENT DOCUMENTS

| 3,042,044 A | 7/1962 | Sheridan |
| 3,400,714 A | 9/1968 | Sheridan |

(Continued)

FOREIGN PATENT DOCUMENTS

| CN | 103068435 A | 4/2013 |
| EP | 2603275 A2 | 6/2013 |

(Continued)

OTHER PUBLICATIONS

CN 201180039622.X filed Feb. 16, 2013 First Office Action dated Aug. 4, 2014.
(Continued)

*Primary Examiner* — Jason E Flick
(74) *Attorney, Agent, or Firm* — Rutan & Tucker LLP

(57) ABSTRACT

A catheter for insertion into a body of a patient, and methods of making and using. The catheter can include a distal portion that remains stable during fluid infusion into the patient, thus reducing or eliminating whipping of the catheter distal tip. The catheter can include a proximal portion including a first cross sectional lumen area; a distal portion including a second cross sectional lumen area larger than the first cross sectional lumen area such that the distal portion prevents whipping when the catheter is disposed in a patient and a fluid exits the catheter. The catheter can be attached to a vascular access port and a method can include power injecting a fluid through the vascular access port and the catheter.

9 Claims, 17 Drawing Sheets

Related U.S. Application Data continuation of application No. 15/002,335, filed on Jan. 20, 2016, now Pat. No. 10,238,833, which is a continuation-in-part of application No. 13/209,270, filed on Aug. 12, 2011, now Pat. No. 9,913,960.

(60) Provisional application No. 61/373,000, filed on Aug. 12, 2010.

(52) U.S. Cl.
CPC ....... *A61M 25/001* (2013.01); *A61M 25/0009* (2013.01); *A61M 25/0023* (2013.01); *A61M 25/0054* (2013.01); *A61M 25/0068* (2013.01); *A61M 25/0071* (2013.01); *A61M 2025/0024* (2013.01); *A61M 2025/0031* (2013.01); *A61M 2025/0035* (2013.01); *A61M 2025/0037* (2013.01); *A61M 2025/0059* (2013.01); *A61M 2207/00* (2013.01)

(58) Field of Classification Search
CPC ...... A61M 2025/0059; A61M 2207/00; A61M 25/0009; A61M 25/001; A61M 25/0023; A61M 25/003; A61M 25/0043; A61M 25/0054; A61M 25/0068; A61M 25/0071; A61M 25/008; A61M 25/00; A61M 25/0021; A61M 2207/10; A61M 25/0067
See application file for complete search history.

(56) References Cited

U.S. PATENT DOCUMENTS

| | | |
|---|---|---|
| 3,687,142 A | 8/1972 | Leibinzohn |
| 4,345,602 A | 8/1982 | Yoshimura et al. |
| 4,547,193 A | 10/1985 | Rydell |
| 4,563,180 A | 1/1986 | Jervis et al. |
| 4,735,620 A | 4/1988 | Ruiz |
| 4,769,016 A | 9/1988 | Labianca |
| 4,846,814 A | 7/1989 | Ruiz |
| 4,871,356 A | 10/1989 | Haindl et al. |
| 4,961,731 A | 10/1990 | Bodicky et al. |
| 4,961,809 A | 10/1990 | Martin |
| 5,041,083 A | 8/1991 | Tsuchida et al. |
| 5,085,635 A | 2/1992 | Cragg |
| 5,127,917 A | 7/1992 | Niederhauser et al. |
| 5,163,431 A | 11/1992 | Griep |
| 5,178,803 A | 1/1993 | Tsuchida et al. |
| 5,180,364 A | 1/1993 | Ginsburg |
| 5,201,723 A | 4/1993 | Quinn |
| 5,234,425 A | 8/1993 | Fogarty et al. |
| 5,292,305 A | 3/1994 | Boudewijn et al. |
| 5,316,706 A | 5/1994 | Muni et al. |
| 5,395,353 A | 3/1995 | Scribner |
| 5,399,168 A | 3/1995 | Wadsworth, Jr. et al. |
| 5,509,900 A | 4/1996 | Kirkman |
| 5,531,717 A | 7/1996 | Roberto et al. |
| 5,533,985 A | 7/1996 | Wang |
| 5,571,093 A | 11/1996 | Cruz et al. |
| 5,578,006 A | 11/1996 | Schon |
| 5,616,137 A | 4/1997 | Lindsay |
| 5,643,228 A | 7/1997 | Schucart et al. |
| 5,707,385 A | 1/1998 | Williams |
| 5,735,832 A | 4/1998 | Karlsson |
| 5,807,349 A | 9/1998 | Person et al. |
| 5,830,196 A | 11/1998 | Hicks |
| 5,843,017 A | 12/1998 | Yoon |
| 5,857,464 A | 1/1999 | Desai |
| 5,902,282 A | 5/1999 | Balbierz |
| 5,931,831 A | 8/1999 | Linder |
| 5,938,635 A | 8/1999 | Kuhle |
| 5,961,536 A | 10/1999 | Mickley et al. |
| 5,976,120 A | 11/1999 | Chow et al. |
| 5,989,206 A | 11/1999 | Prosl et al. |
| 6,010,494 A | 1/2000 | Schafer et al. |
| 6,045,547 A | 4/2000 | Ren et al. |
| 6,052,612 A | 4/2000 | Desai |
| 6,059,748 A | 5/2000 | Teirstein et al. |
| 6,059,760 A | 5/2000 | Sandmore et al. |
| 6,074,379 A | 6/2000 | Prichard |
| 6,090,072 A | 7/2000 | Kratoska et al. |
| 6,096,022 A | 8/2000 | Laymon et al. |
| 6,129,700 A | 10/2000 | Fitz |
| 6,132,405 A | 10/2000 | Nilsson et al. |
| 6,192,568 B1 | 2/2001 | Kafrawy et al. |
| 6,203,532 B1 | 3/2001 | Wright |
| 6,217,565 B1 | 4/2001 | Cohen |
| 6,280,423 B1 | 8/2001 | Davey et al. |
| 6,280,434 B1 | 8/2001 | Kinoshita et al. |
| 6,293,958 B1 | 9/2001 | Berry et al. |
| 6,450,987 B1 | 9/2002 | Kramer |
| 6,482,211 B1 | 11/2002 | Choi |
| 6,524,299 B1 | 2/2003 | Tran et al. |
| 6,533,750 B2 | 3/2003 | Sutton et al. |
| 6,533,763 B1 | 3/2003 | Schneiter |
| 6,579,306 B1 | 6/2003 | Voelker et al. |
| 6,579,484 B1 | 6/2003 | Tiernan et al. |
| 6,595,966 B2 | 7/2003 | Davey et al. |
| 6,620,118 B1 | 9/2003 | Prosl et al. |
| 6,626,859 B2 | 9/2003 | von Segesser |
| 6,638,242 B2 | 10/2003 | Wilson et al. |
| 6,638,266 B2 | 10/2003 | Wilson et al. |
| 6,651,477 B2 | 11/2003 | Humphries et al. |
| 6,663,614 B1 | 12/2003 | Carter |
| 6,669,679 B1 | 12/2003 | Savage et al. |
| 6,858,024 B1 | 2/2005 | Berg et al. |
| 6,866,655 B2 | 3/2005 | Hackett |
| 6,872,198 B1 | 3/2005 | Wilson et al. |
| 6,921,396 B1 | 7/2005 | Wilson et al. |
| 6,984,219 B2 | 1/2006 | Ashby et al. |
| 7,025,751 B2 | 4/2006 | Silva et al. |
| 7,037,295 B2 | 5/2006 | Tiernan et al. |
| 7,112,191 B2 | 9/2006 | Daga |
| 7,128,734 B1 | 10/2006 | Wilson et al. |
| 7,137,963 B2 | 11/2006 | Nita et al. |
| 7,300,430 B2 | 11/2007 | Wilson et al. |
| 7,381,204 B2 | 6/2008 | Wilson et al. |
| 7,393,339 B2 | 7/2008 | Zawacki et al. |
| 7,410,602 B2 | 8/2008 | Davey et al. |
| 7,566,316 B2 | 7/2009 | McGuckin, Jr. et al. |
| 7,566,342 B2 | 7/2009 | Parker et al. |
| 7,582,051 B2 | 9/2009 | Khairkhahan et al. |
| 7,682,353 B2 | 3/2010 | Tanghoj et al. |
| 7,686,800 B2 | 3/2010 | Savage et al. |
| 7,722,567 B2 | 5/2010 | Tal |
| 7,749,185 B2 | 7/2010 | Wilson et al. |
| 7,799,046 B2 | 9/2010 | White et al. |
| 7,833,214 B2 | 11/2010 | Wilson et al. |
| 7,846,134 B1 | 12/2010 | Nadolski et al. |
| 7,867,271 B2 | 1/2011 | Geiser et al. |
| 7,871,398 B2 | 1/2011 | Chesnin et al. |
| 7,955,293 B2 | 6/2011 | Nita et al. |
| 7,985,213 B2 | 7/2011 | Parker |
| 8,034,072 B2 | 10/2011 | Nguyen et al. |
| 8,603,067 B2 | 12/2013 | Lareau et al. |
| 9,913,960 B2 | 3/2018 | Blanchard et al. |
| 10,238,833 B2 | 3/2019 | Christian et al. |
| 2001/0001117 A1 | 5/2001 | Chow |
| 2001/0018576 A1 | 8/2001 | Quinn |
| 2001/0051786 A1 | 12/2001 | Davey et al. |
| 2002/0072706 A1 | 6/2002 | Hiblar et al. |
| 2002/0099326 A1 | 7/2002 | Wilson et al. |
| 2003/0018322 A1 | 1/2003 | Tanghoj et al. |
| 2003/0036698 A1 | 2/2003 | Kohler et al. |
| 2003/0153873 A1 | 8/2003 | Luther et al. |
| 2003/0236545 A1 | 12/2003 | Gilson |
| 2004/0073122 A1* | 4/2004 | Stofer .................. A61B 5/031 600/488 |
| 2004/0073171 A1 | 4/2004 | Rogers et al. |
| 2004/0097905 A1 | 5/2004 | Savage et al. |
| 2004/0171997 A1 | 9/2004 | Wilson et al. |
| 2004/0193139 A1 | 9/2004 | Armstrong et al. |
| 2004/0199192 A1 | 10/2004 | Akahoshi |
| 2004/0249338 A1 | 12/2004 | DeCant et al. |

(56) References Cited

U.S. PATENT DOCUMENTS

| | | |
|---|---|---|
| 2005/0027262 A1 | 2/2005 | Appling et al. |
| 2005/0038411 A1 | 2/2005 | Okada |
| 2005/0043649 A1 | 2/2005 | Urie |
| 2005/0080406 A1 | 4/2005 | Malecki et al. |
| 2005/0085778 A1 | 4/2005 | Parks |
| 2005/0090780 A1 | 4/2005 | Stone |
| 2005/0124969 A1* | 6/2005 | Fitzgerald ............ A61B 5/0086 604/35 |
| 2005/0187535 A1 | 8/2005 | Wilson et al. |
| 2005/0209581 A1 | 9/2005 | Butts et al. |
| 2006/0004316 A1 | 1/2006 | Difiore et al. |
| 2006/0041244 A1 | 2/2006 | Hohmann et al. |
| 2006/0041269 A1 | 2/2006 | Horrigan |
| 2006/0281965 A1 | 12/2006 | Khairkhahan et al. |
| 2007/0043390 A1 | 2/2007 | Neilan |
| 2007/0060880 A1 | 3/2007 | Gregorich et al. |
| 2007/0073271 A1 | 3/2007 | Brucker et al. |
| 2007/0219466 A1 | 9/2007 | Tremulis et al. |
| 2007/0225661 A1 | 9/2007 | Ash et al. |
| 2008/0172008 A1 | 7/2008 | Root et al. |
| 2009/0012481 A1 | 1/2009 | Davey et al. |
| 2009/0093795 A1 | 4/2009 | Koeper |
| 2009/0131882 A1 | 5/2009 | Naimark et al. |
| 2009/0143748 A1 | 6/2009 | Mickley et al. |
| 2009/0221961 A1 | 9/2009 | Tal et al. |
| 2009/0247987 A1 | 10/2009 | Chevalier, Jr. et al. |
| 2009/0254116 A1 | 10/2009 | Rosenschein et al. |
| 2009/0292272 A1 | 11/2009 | McKinnon |
| 2009/0306606 A1 | 12/2009 | Lancette et al. |
| 2009/0312687 A1 | 12/2009 | DeFonzo et al. |
| 2011/0034875 A1 | 2/2011 | Chesnin et al. |
| 2011/0202002 A1 | 8/2011 | Gordon et al. |
| 2011/0213309 A1 | 9/2011 | Young et al. |
| 2011/0213318 A1 | 9/2011 | Schertiger |
| 2012/0016311 A1 | 1/2012 | Altman et al. |
| 2012/0041419 A1 | 2/2012 | Blanchard et al. |
| 2012/0232496 A1 | 9/2012 | Lareau et al. |
| 2012/0245563 A1 | 9/2012 | Lareau et al. |
| 2015/0289781 A1 | 10/2015 | Grunwald et al. |
| 2019/0217056 A1 | 7/2019 | Christian et al. |

FOREIGN PATENT DOCUMENTS

| | | |
|---|---|---|
| WO | 1996/006653 A1 | 3/1996 |
| WO | 96/39217 A1 | 12/1996 |
| WO | 2004030577 A1 | 4/2004 |
| WO | 2009/131583 A1 | 10/2009 |
| WO | 2009/142904 A1 | 11/2009 |
| WO | 2010020971 A2 | 2/2010 |
| WO | 2010039456 A1 | 4/2010 |
| WO | 2010/054666 A1 | 5/2010 |
| WO | 2012021844 A2 | 2/2012 |
| WO | 2017/127074 A1 | 7/2017 |

OTHER PUBLICATIONS

CN 201180039622.X filed Feb. 16, 2013 second Office Action dated May 15, 2015.
CN 201180039622.X filed Feb. 16, 2013 Third Office Action dated Oct. 10, 2015.
EP 11817136.2 filed Jan. 24, 2014 Extended European Search Report, dated Sep. 19, 2017.
EP 16886714.1 filed Aug. 20, 2018 Extended European Search Report dated Aug. 30, 2019.
KR 10-2013-7006208 filed Mar. 11, 2013 Office Action dated Jan. 9, 2018.
KR 10-2013-7006208 filed Mar. 11, 2013 Office Action dated Jul. 30, 2018.
MX/a/2013/000715 filed Jan. 17, 2013 First Office Action dated Feb. 12, 2015.
MX/a/2013/000715 filed Jan. 17, 2013 Second Office Action dated Jun. 4, 2015.
MX/a/2013/000715 filed Jan. 17, 2013 Third Office Action dated Oct. 12, 2015.
PCT/US2011/047656 filed Aug. 12, 2011 International Search Report and Written Opinion dated Mar. 9, 2012.
PCT/US2016/014190 filed Jan. 20, 2016 International Search Report and Written Opinion dated Mar. 29, 2016.
Silverstein, Beth et al., Abstract, "Assessing the Role of the Biomaterial Aquavene in Patient Reactions to Landmark Midline Catheters," Regulatory Toxicology and Pharmacology, vol. 25, Issue 1, pp. 60-67, Feb. 1997.
U.S. Appl. No. 13/209,270, filed Aug. 12, 2011 Final Office Action dated Jul. 10, 2014.
U.S. Appl. No. 13/209,270, filed Aug. 12, 2011 Final Office Action dated May 27, 2015.
U.S. Appl. No. 13/209,270, filed Aug. 12, 2011 Non-Final Office Action dated Feb. 26, 2014.
U.S. Appl. No. 13/209,270, filed Aug. 12, 2011 Non-Final Office Action dated Jan. 14, 2015.
U.S. Appl. No. 13/209,270, filed Aug. 12, 2011 Non-Final Office Action dated Oct. 25, 2013.
U.S. Appl. No. 13/209,270, filed Aug. 12, 2011 Notice of Allowance dated Nov. 15, 2017.
U.S. Appl. No. 13/474,004, filed May 17, 2012 Final Office Action dated May 8, 2013.
U.S. Appl. No. 13/474,004, filed May 17, 2012 Final Office Action dated Oct. 19, 2012.
U.S. Appl. No. 13/474,004, filed May 17, 2012 Non-Final Office Action dated Dec. 27, 2012.
U.S. Appl. No. 13/474,004, filed May 17, 2012 Non-Final Office Action dated Jul. 13, 2012.
U.S. Appl. No. 13/474,004, filed May 17, 2012 Notice of Allowance dated Sep. 12, 2013.
U.S. Appl. No. 15/002,335, filed Jan. 20, 2016 Non-Final Office Action dated May 25, 2018.
U.S. Appl. No. 15/002,335, filed Jan. 20, 2016 Restriction Requirement dated May 2, 2018.
U.S. Appl. No. 16/362,531, filed Mar. 22, 2019 Notice of Allowance dated Oct. 30, 2020.
EP 22195818.4 filed Extended European Search Report dated Nov. 30, 2022.

* cited by examiner

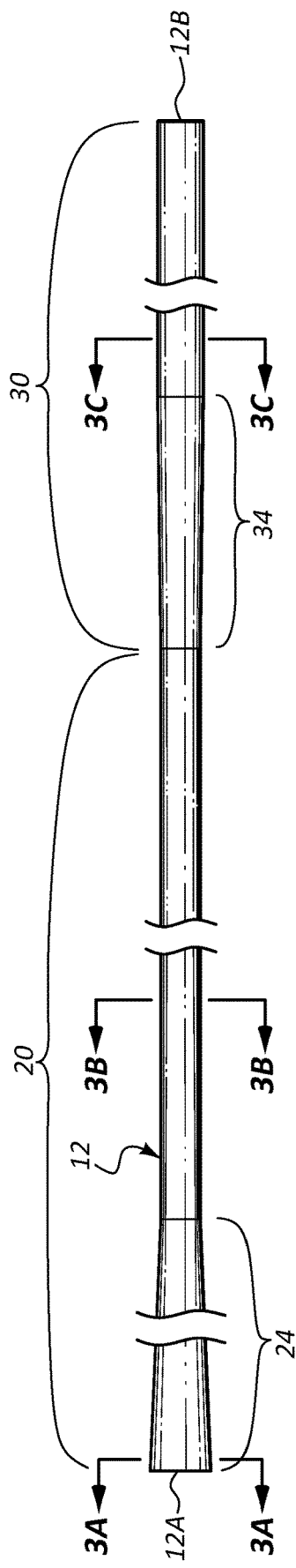
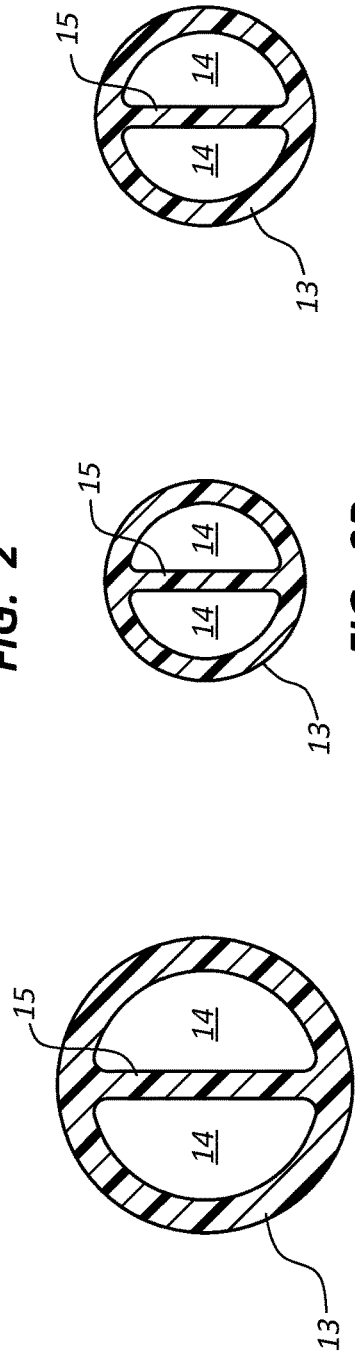
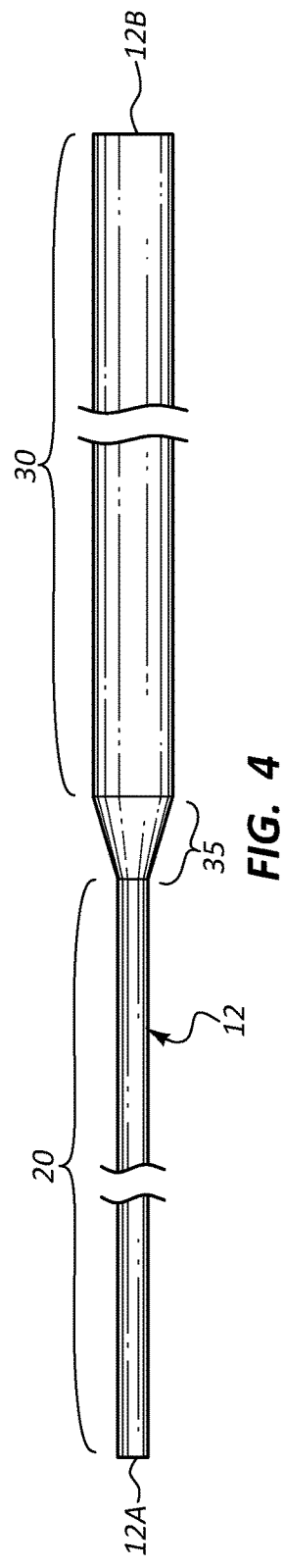
FIG. 2
FIG. 3A
FIG. 3B
FIG. 3C
FIG. 4

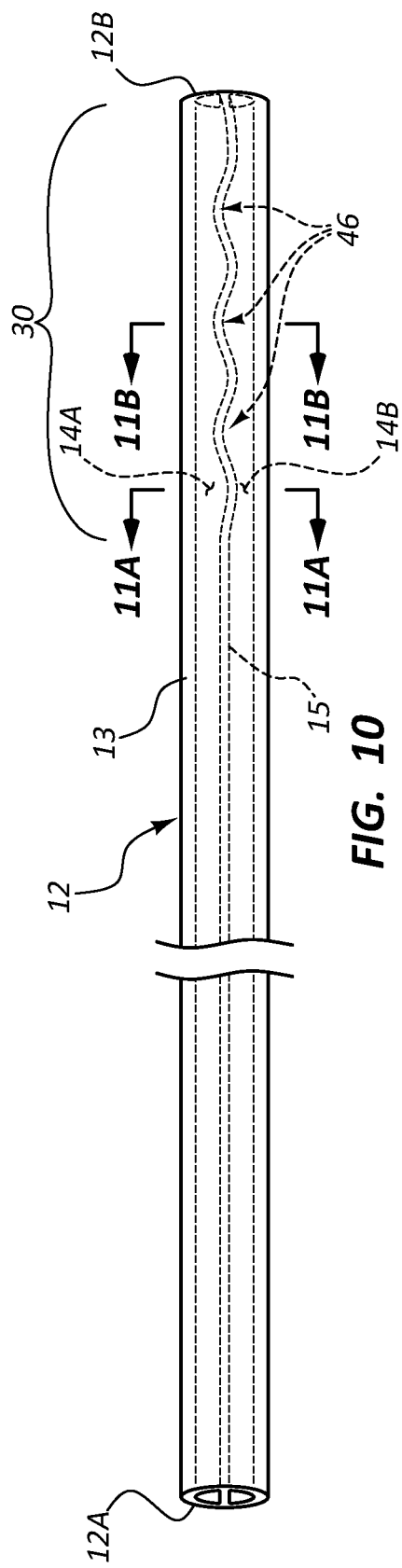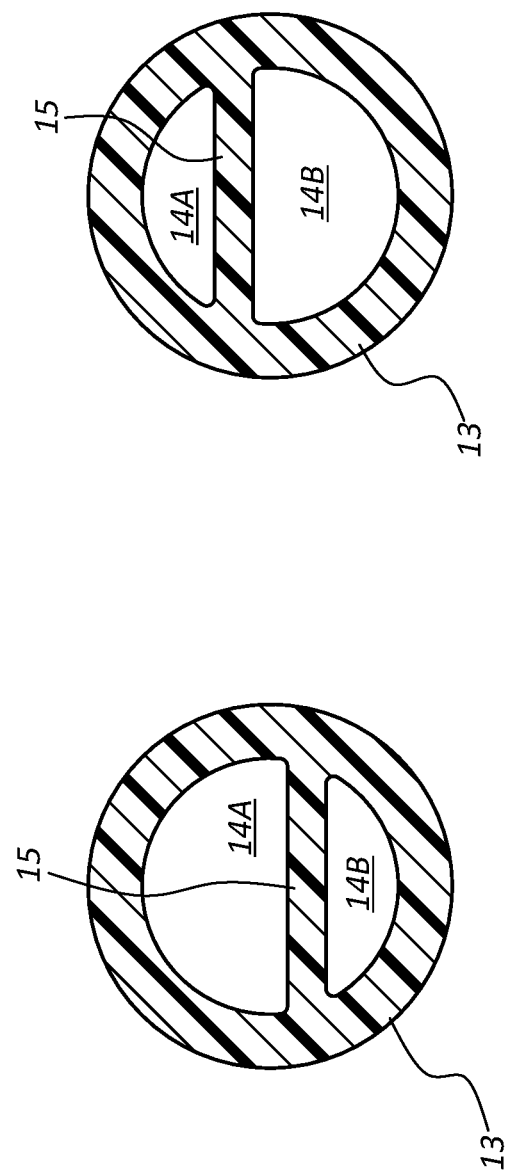

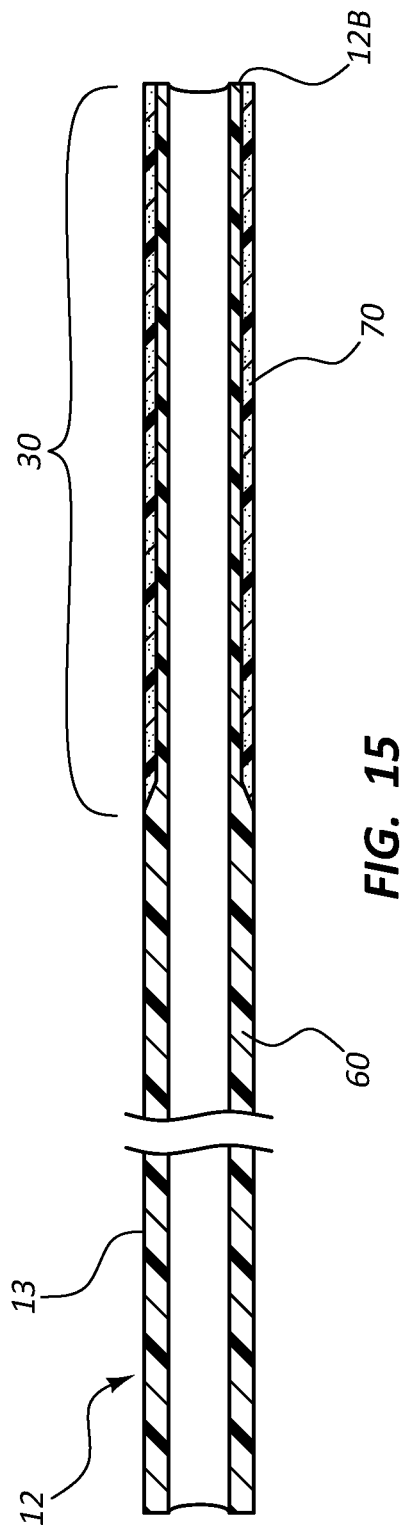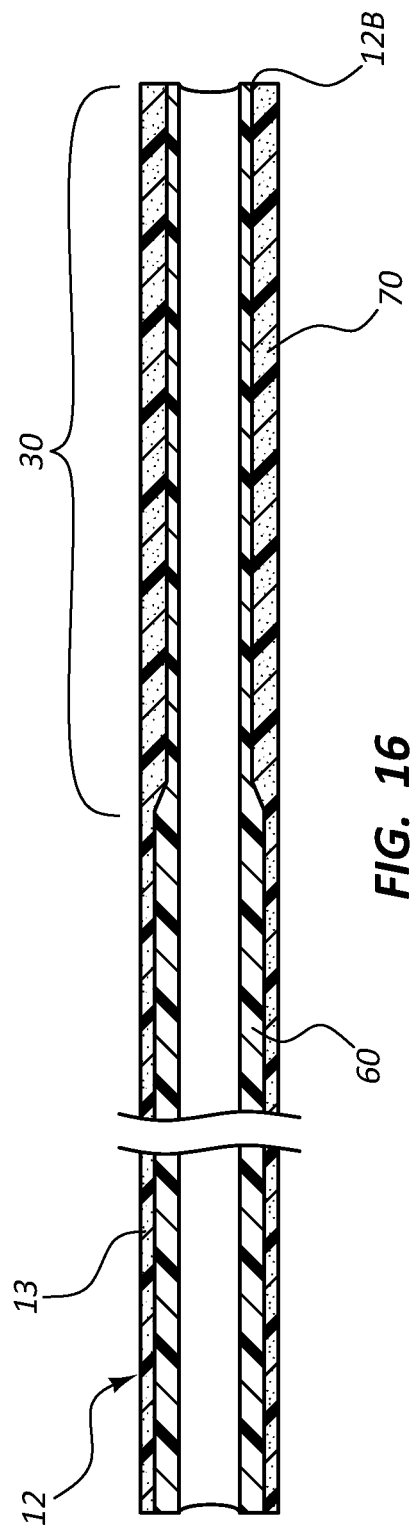

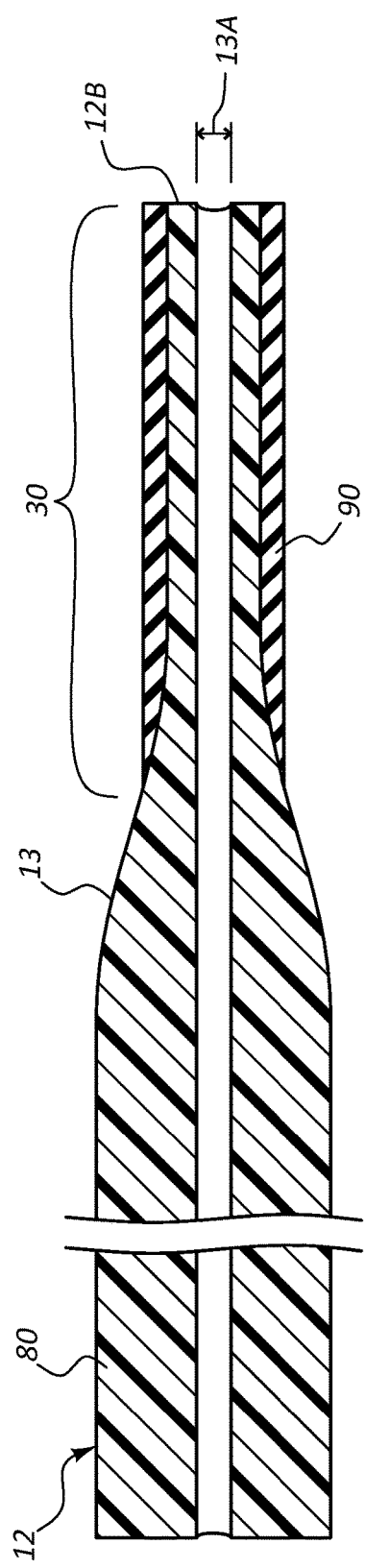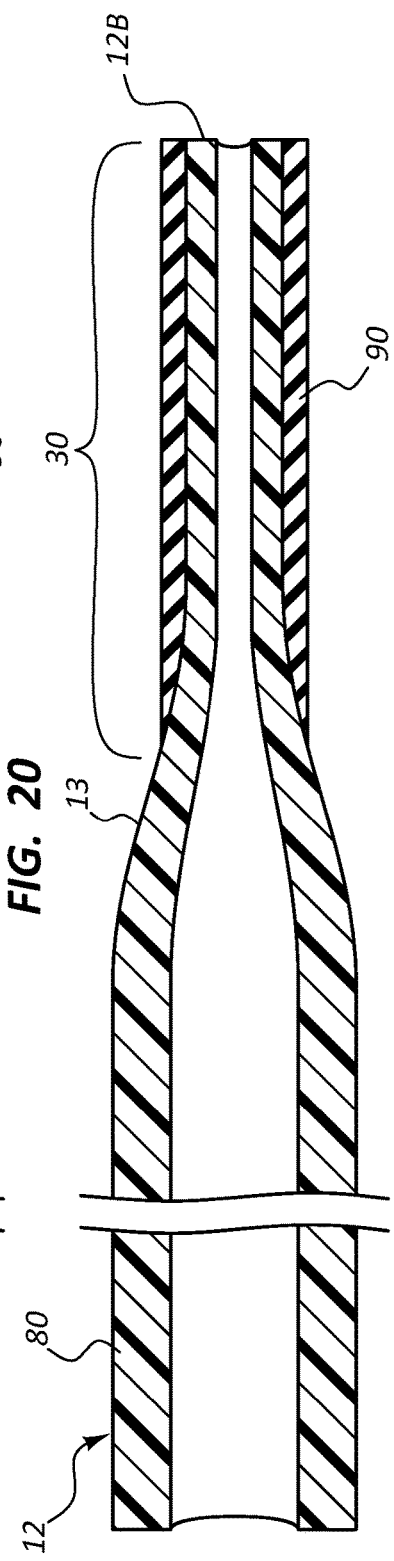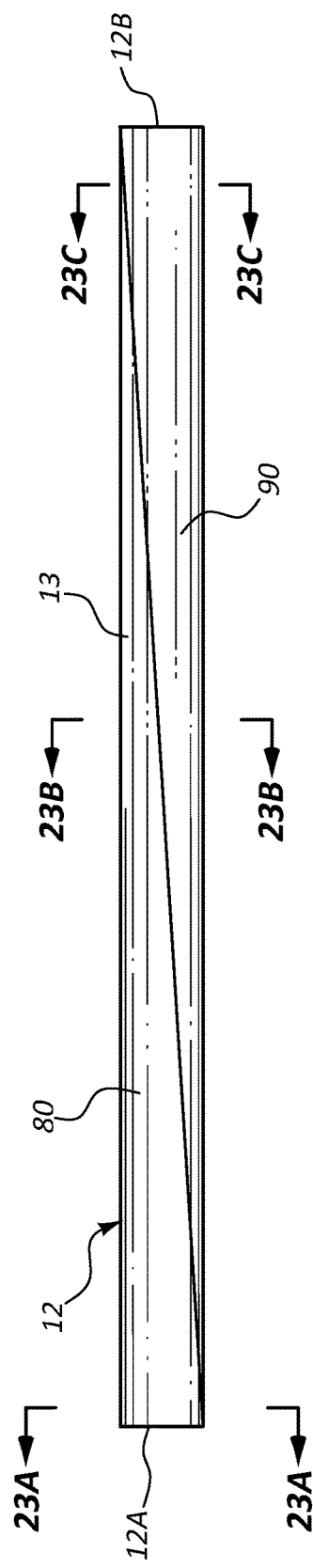

ACCESS PORT AND CATHETER ASSEMBLY INCLUDING CATHETER DISTAL PORTION STABILITY FEATURES

CROSS-REFERENCE TO RELATED APPLICATIONS

This application is a continuation of U.S. patent application Ser. No. 16/362,531, filed Mar. 22, 2019, now U.S. Pat. No. 10,905,850, which is a continuation of U.S. patent application Ser. No. 15/002,335, filed Jan. 20, 2016, now U.S. Pat. No. 10,238,833, which is a continuation-in-part of U.S. patent application Ser. No. 13/209,270, filed Aug. 12, 2011, now U.S. Pat. No. 9,913,960, which claims the benefit of U.S. Provisional Patent Application No. 61/373,000, filed Aug. 12, 2010, each of which is incorporated herein by reference in its entirety.

BRIEF SUMMARY

Briefly summarized, embodiments of the present invention are directed to a catheter assembly used to gain access to a vasculature or other internal portion of a patient. The catheter assembly includes a catheter tube that defines one or more lumens, with at least one lumen optionally capable of power injection, in one embodiment. A proximal portion of the catheter tube is sized and configured so as to reside within a portion of the vessel that is disposed relatively close to the insertion site of the catheter tube into the patient. In particular, as such portions of the vessel are of relatively small diameter, the proximal portion of the catheter tube is similarly of relatively small diameter and of relatively low stiffness so as to prevent substantial occlusion of the vessel by the catheter tube and lessen vessel damage.

Moreover, a distal portion of the catheter tube is sized and configured such that the distal portion remains stable within the vessel during infusion of fluids therethrough. Particularly, the distal portion of the catheter tube is configured to avoid whipping of the distal tip within the vessel during fluid infusion so as to prevent vessel damage. This stability of the catheter tube's distal portion is especially helpful during power injection of fluids into the vessel.

In one embodiment, stability of the distal tip of the catheter tube is accomplished by flaring, or increasing the cross sectional size of the distal portion of the tube, thus increasing the areal size of the one or more catheter lumens and improving the area moment of inertia of the distal portion. In another embodiment, the elastic modulus, or stiffness, of the distal portion can be increased relative to the proximal portion of the catheter tube. In another embodiment, both the area moment of inertia and the modulus can be modified to enhance distal portion stability. Note that these and related parameters can be modified in other ways as well.

Thus, in one embodiment, a catheter tube for insertion into a body of a patient is disclosed. The catheter tube includes a distal portion that remains stable during fluid infusion into the patient, thus reducing or eliminating whipping of the catheter distal tip, even during power injection. In one embodiment, the catheter tube defines at least one lumen and is formed from a tube material that defines a proximal portion and a distal portion of the catheter tube. The catheter tube is configured such that the arithmetic product of an elastic modulus and an area moment of inertia for at least a portion of the distal portion of the catheter tube defined by the catheter tube material is greater relative the arithmetic product of an elastic modulus and an area moment of inertia for at least a portion of the proximal portion of the catheter tube.

In another embodiment, an implantable vascular access port system is disclosed, wherein a stabilized catheter tube similar to that described above is operably connected to an implantable access port, such as an arm port, for instance. These and other uses of the stabilized catheter tube, such as its use as a PICC or other catheter assembly for providing external access to a patient's vasculature, are contemplated.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 2 is a side view of the catheter tube of the assembly shown in FIG. 1;

FIGS. 3A-3C are cross sectional views of the catheter tube of FIG. 2, showing a relative change in catheter tube structure;

FIG. 4 is a side view of a catheter tube configured in accordance with one embodiment;

FIG. 10 is a side view of a catheter tube in accordance with one embodiment;

FIGS. 11A and 11B are cross sectional views of the catheter tube of FIG. 10;

FIG. 15 is a cross sectional side view of a catheter tube in accordance with one embodiment;

FIG. 16 is a cross sectional side view of a catheter tube in accordance with one embodiment;

FIG. 20 is a cross sectional side view of a catheter tube in accordance with one embodiment;

FIG. 21 is a cross sectional side view of a catheter tube in accordance with one embodiment;

FIG. 22 is a side view of a catheter tube in accordance with one embodiment;

DETAILED DESCRIPTION OF SELECTED EMBODIMENTS

Figure 1:
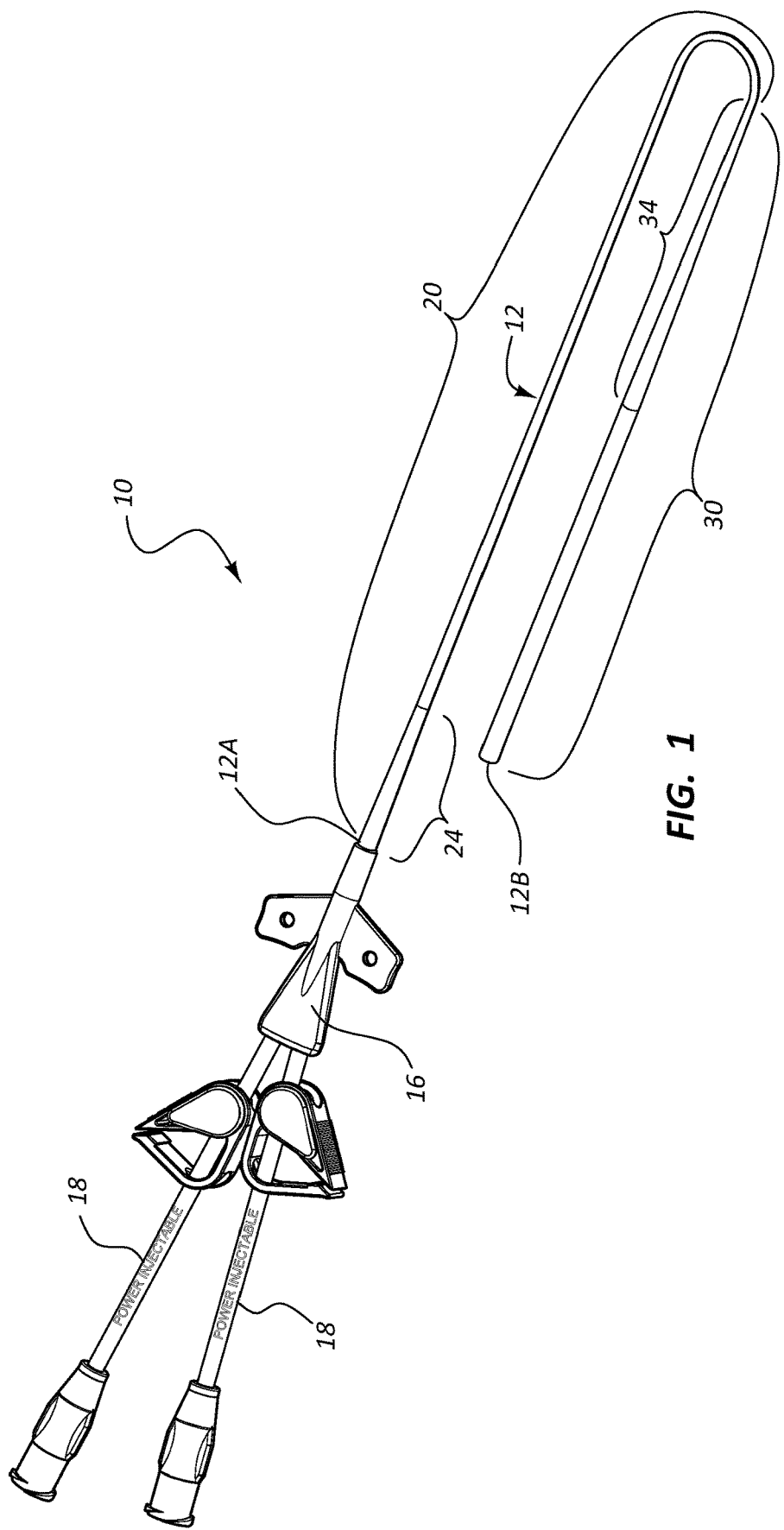
FIG. 1 is a perspective view of a catheter assembly configured in accordance with one embodiment.

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a catheter assembly used to gain access to a vasculature or other internal portion of a patient. The catheter assembly includes a catheter tube that defines one or more lumens, with at least one lumen capable of power injection, in one embodiment. A proximal portion of the catheter tube is sized and configured so as to reside within a portion of the vessel that is disposed relatively close to the insertion site of the catheter tube into the patient. In particular, as such portions of the vessel are of relatively small diameter, the proximal portion of the catheter tube is similarly of relatively small diameter and of relatively low stiffness so as to enable ease of passage of the catheter tube through the vessel and to prevent substantial occlusion of the vessel by the catheter tube Moreover, a distal portion of the catheter tube is sized and configured such that it remains stable within the vessel during infusion of fluids therethrough. Particularly, the distal portion of the catheter tube is configured to avoid whipping of the distal tip within the vessel during fluid infusion so as to prevent vessel damage. This stability of the catheter tube's distal portion is especially helpful during power injection of fluids into the vessel.

In one embodiment, stability of the distal tip of the catheter tube is accomplished by flaring, or increasing the cross sectional size of the distal portion of the tube thus increasing the areal size of the one or more catheter lumens and improving the moment area of inertia of the distal portion. In another embodiment, the elastic modulus, or stiffness, of the distal portion can be increased relative to the proximal portion of the catheter tube. In another embodiment, both the moment area of inertia and the modulus can be modified to enhance distal portion stability. Note that these and related parameters can be modified in other ways as well and that additional configurations for increasing distal tip stability are disclosed. In addition to the catheter tubes described herein as part of catheter assemblies, the principles to be disclosed can be employed with other tubular medical devices as well.

Reference is first made to FIG. 1, which depicts various details of a catheter assembly, generally designated at 10, according to one embodiment. As shown, the catheter assembly ("catheter") 10 includes an elongate catheter tube 12 formed by an outer wall 13 which, together with a septum 15 (FIGS. 3A-3C) defines one or more lumens 14 extending between a proximal end 12A and a distal end 12B of the tube. A bifurcation 16 mates with the catheter tube 12 at the proximal end 12A thereof to provide fluid communication between the catheter tube and one or more extension legs 18.

FIG. 2 shows further details of the catheter tube of the catheter 10, according to the present embodiment. As shown, the tube 12 includes a proximal portion 20 extending distally from the proximal end 12A and a distal portion 30 extending distally from the distal end of the proximal portion to the distal end 12B of the tube. A tapered region 24 of the proximal portion 20 is included in the catheter tube 12 and is configured such that the thickness of the outer wall 13 and septum 15 decrease from the tube proximal end 12A to the distal termination of the tapered region 24. In addition, the areal size of each of the lumens 14 also decreases distally over this region. These size differences can be seen by comparing FIGS. 3A and 3B, which show cross sectional views of the catheter tube 12 at the proximal end of the tapered region 24 (FIG. 3A) and distal to the distal termination of the tapered region (FIG. 3B).

The proximal tapered region 24 provides sufficient outer wall thickness and rigidity for the catheter tube 12 of the present embodiment so as to prevent kinking and to enable the tube to be adjusted with respect to an insertion site in the skin of the patient during insertion and adjustment of the catheter 10. Furthermore, the proximal tapered region 24 serves to plug the insertion site through which the catheter tube passes into the patient's body, thus reducing bleeding or other complications at the site.

The remainder of the proximal portion 20 of the catheter tube 12 resides within distal portions of the vessel that are typically located relatively close to the catheter insertion site in extremities of the patient, such as the arm. Such outlying, or distal, vessels are relatively smaller than the larger vessels located deeper within the body in which the distal portion 30 of the catheter tube 12 is disposed. Thus, the proximal portion 20 of the catheter tube 12 distal to the tapered region 24 is similarly sized relatively small so that this portion can reside in the relatively small vessel without occluding a significant portion thereof, which in turn reduces the risk of thrombus. Further, the smaller size of the proximal portion 20 enables it to bend more easily during insertion into the vessel along a potentially tortuous path, resulting in less trauma and damage to the vessel.

As best seen in FIG. 2, the distal portion 30 of the catheter tube 12 includes a distal taper region 34 that provides a size transition for the tube from the distal end of the proximal portion 20 and the remainder of the distal portion 30. Specifically, the distal taper region 34 enables the dimensions of the catheter tube 12 to change from the cross sectional configuration corresponding to the proximal portion 20 shown in FIG. 3B to that of the distal portion 30 shown in FIG. 3C, wherein the thickness of the outer wall 13 and septum 15, together with the areal size of the lumens 14, increase. This general size increase of the catheter tube distal portion 30 provides enhanced stability for this portion of the catheter tube 12, which in turn prevents oscillatory movement, or whipping, of the distal tip of the tube during fluid infusion through the catheter into the vessel in which the catheter 10 is disposed. This in turn reduces the chance for vessel wall damage caused by repetitive impacts of the whipping catheter tube.

In greater detail, it is appreciated that an unsupported stable length, L, of a distal portion of a catheter tube can be characterized by:

$$L = \frac{c}{Q}\sqrt{\frac{EIA}{\rho}}, \quad (1)$$

where $\rho$ is the density of the injected fluid, Q is the flow rate of the injected fluid, A is the cross sectional lumen area of the catheter tube, E is the elastic modulus of the catheter tube material from which the outer wall 13 and septum 15 are formed, I is the area moment of inertia of the outer wall and septum material, and c is a constant of proportionality.

From equation (1), it is seen that the stability length L of the catheter tube 12 can be increased by increasing one or more of the parameters E, I, and A. The increased size of the distal portion 30 of the catheter tube 12 and the portions of the lumens 14 it defines (FIGS. 1 and 2) serves to increase both the area moment of inertia I and the lumen area A, which in turn improves the stability length L, which corresponds to a more stable tip within the vessel during fluid injection. This tip stability of the distal portion 30 of the catheter tube 12 is especially helpful during power injection of fluids into the vessel, where catheter fluid flow rate Q can exceed about 5 cc/second. Under such conditions, the ability to preserve tip stability and reduce or eliminate tip whipping is especially beneficial.

As discussed above, an increase in the size of the distal portion 30 and/or other portions of the catheter tube 12 increases the area moment of inertia I and thus improves tip stability. Note that I is directly related by the fourth power of the radius of the catheter tube. As such, a relatively small increase in the cross sectional size of the catheter tube can have a significant effect on I, which enhances distal tip stability. Further note that I can be beneficially improved by increasing the thickness of the outer wall and/or septum of the catheter tube while not increasing the area A of the lumen(s) of the tube.

Also, the flexural stiffness, defined as the product of the parameters E and I, is higher in the distal portion 30 relative to that of the proximal portion 20, in one embodiment, in order to provide distal tip stability during fluid infusion. This can be accomplished by increasing the elastic modulus and/or the area moment of inertia for the distal portion over that of the proximal portion in any one of the ways discussed herein, or in other ways contemplated by one skilled in the art.

Again as discussed above, an increase in the size of the distal portion 30 and/or other portions of the catheter tube 12 increases the area A of the lumens 14 and thus improves tip stability. Note that in other embodiments lumen area A can be desirably increased in other ways as well, including: a thinning of the outer wall and septum while taking care not to reduce the area moment of inertia A of the distal portion; increasing the lumen area while maintaining the outer diameter of the catheter tube constant, etc.

Though it can be formed to a variety of lengths to suit different uses and applications, in one embodiment the proximal taper region 24 of the proximal portion 20 is about 4 cm in length, the remainder of the proximal portion is about 20 to about 25 cm, the distal taper region 34 of the distal portion 30 is about 4 cm, and the remainder of the distal portion is about 35 cm. Of course, other lengths for the various segments described above can be employed.

Moreover, the lengths, cross sectional sizes of, and relative size differences between the various segments can also vary from what is shown and described herein, as appreciated by one skilled in the art. In the present embodiment, the approximate diameter, wall thickness, and septum thickness (in inches) for each of the cross section views shown in FIGS. 3A-3C are, respectively: 0.095, 0.011, 0.008 (FIG. 3A); 0.063, 0.0070, 0.0055 (FIG. 3B); and 0.070, 0.0080, 0.0060 inch (FIG. 3C). Note that these are but one possible example of size configurations for the catheter tube 12. Indeed a variety of sizes, including various French sizes, can be employed for the catheter tube. In one embodiment, for example, the proximal catheter portion defines a size in the range of 2-6 French while the distal portion defines a size in the range of 2.5-8 French. It should be further appreciated that the number, size, and other configuration of the catheter lumens can vary from what is shown here. For instance, principles of the present disclosure can be employed with triple and quad lumen catheters. In addition, though the lumens 14 shown in FIGS. 3A-3C are symmetrically arranged, in another embodiment the lumens can be included in an offset configuration so as to provide one or more relatively larger lumens for power injection, if desired.

In this and various other embodiments described herein the catheter tube 12 is extruded or otherwise formed from one or more of a variety of suitable materials, including thermoplastic polyurethanes sold under the trademarks TECOFLEX (type 93AB30) and TECOTHANE (type 95A) of Lubrizol Advanced Materials, Inc., and CARBOTHANE (type 95A), the thermoplastic elastomer sold under the trademark PEBAX of Arkema, Inc., silicone, polyesters, polyethylene, etc. Other suitable materials may also be acceptably used, as appreciated by one skilled in the art.

Note that, though the distal portion of the catheters described here are trimmable, it is desirable that the length of the distal portion remaining after trimming is at least as long as the unsupported stable length L as determined by equation (1), above. In one embodiment, this length is from about 3 to about 10 cm, though other stable lengths are possible, per equation (1).

FIG. 4 shows the catheter tube 12 according to another embodiment, including as before the proximal portion 20 and the distal portion 30 joined by a taper region 35. As shown, the distal portion 30 is flared in size from that of the proximal portion 20, thus providing for enhanced tip stability during power injection or other fluid infusion into the vessel. Note further that, whereas the catheter tube design of FIG. 2 provides for distal trimming of the tube, the catheter tube of FIG. 4 is both proximally and distally trimmable so as to adjust the tube length to the anatomy of the patient. Note that in one embodiment the amount trimmed from the distal end 12B of the catheter tube 12 of FIG. 4 should be such that the remaining portion of the flared distal portion 30 is sufficiently long to ensure distal tip stability during fluid infusion, as suggested by equation (1).

Figure 5:
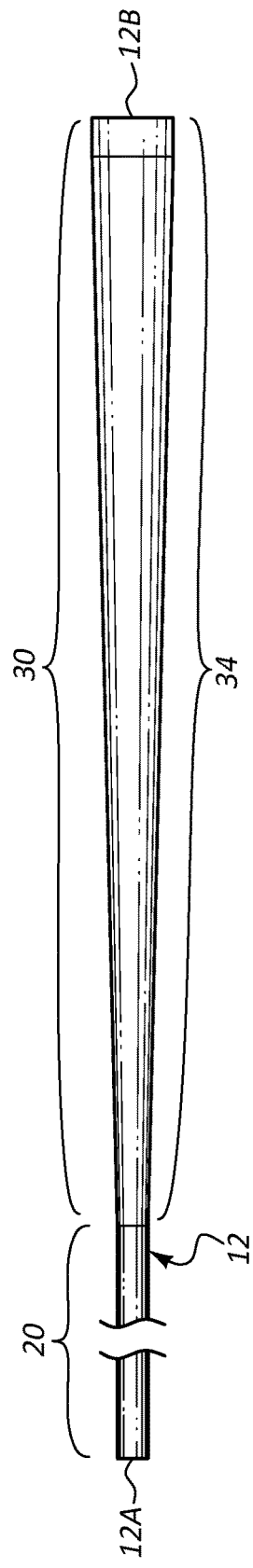
FIG. 5 is a side view of a catheter tube configured in accordance with one embodiment.
Figure 6:
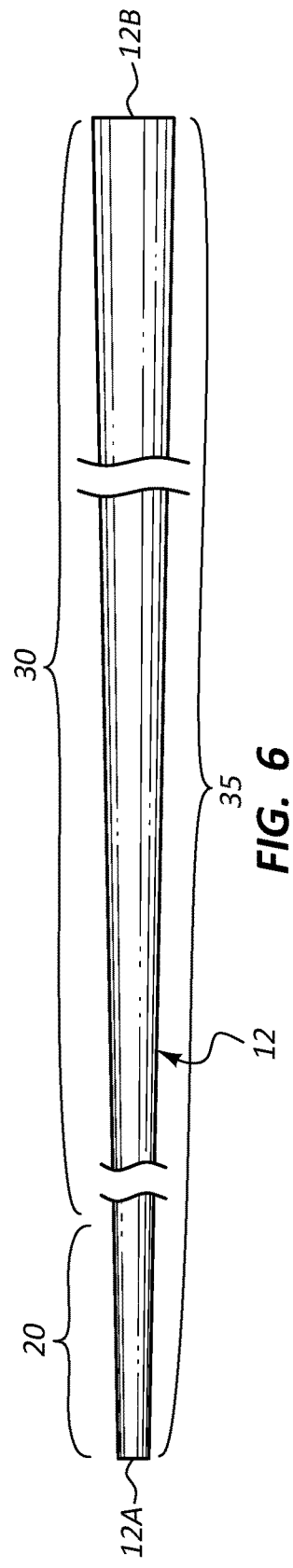
FIG. 6 is a side view of a catheter tube configured in accordance with one embodiment.

FIGS. 5 and 6 give further possible examples of flared catheter tubes 12, wherein the tube of FIG. 5 includes a relatively short proximal portion 20 and a relatively long distal portion 30 extending to the distal tube end 12B. As shown, in this embodiment the entirety of the distal portion 30 serves as the distal taper portion 34 such that the cross sectional size of the distal portion steadily increases toward the distal end of the tube.

In FIG. 6, the taper region 35 extends along the entirety of the length of the catheter tube 12 such that the entire tube includes a taper. As such, both the proximal portion 20 and the distal portion 30 are tapered, or flared. As before, the tapering disclosed in FIGS. 5 and 6 provides for a relatively small and flexible proximal portion suitable for placement in smaller portions of the vessel relatively close to the catheter insertion site, while also providing a stable distal portion that reduced or eliminates distal tip whipping during power injection or other fluid infusion through the distal end of the catheter tube. Such catheter tubes as those described here in connection with FIGS. 5 and 6 or in other embodiments herein can include one, two, or more lumens. Note further that the catheter tube embodiments shown in FIGS. 5 and 6 and in various other embodiments herein are distally trimmable to suit the vasculature of the patient.

With reference to FIGS. 2 and 3C, note that in one embodiment a relationship between the thickness of the outer wall 13 and the cross sectional radius in the distal portion 30 of the catheter tube 12 is established, wherein the outer wall thickness equals about 0.24 multiplied by the outer radius of the catheter tube in the distal portion. So configured, the distal portion 30 offers enhanced distal tip stability during power injection. Put another way, for a single lumen power injectable catheter tube the product of I and A (and hence tube stability) can be maximized where the outer wall thickness of the catheter tube equals about 0.24 of the catheter tube radius in the distal portion thereof. This relationship can be extrapolated for multi-lumen catheter tubes as well. This relationship can be also employed in a catheter tube regardless of whether the distal portion thereof is flared as shown in FIGS. 2, 4, 5, 6, etc. In another embodiment, the outer wall thickness can equal the product of the outer radius of the catheter tube and a number within a range of from about 0.2 to about 0.3.

It is further appreciated that other catheter factors can be adjusted to maximize distal tip stability for the catheter tube 12, including the length of the flared distal portion alone and as a function of overall catheter tube length, the density of the catheter tube material, the degree of flare of the distal portion with respect to non-flared tube portions, the interaction of modulus, area moment of inertia, and lumen area in the flared portion, etc.

Figure 7:
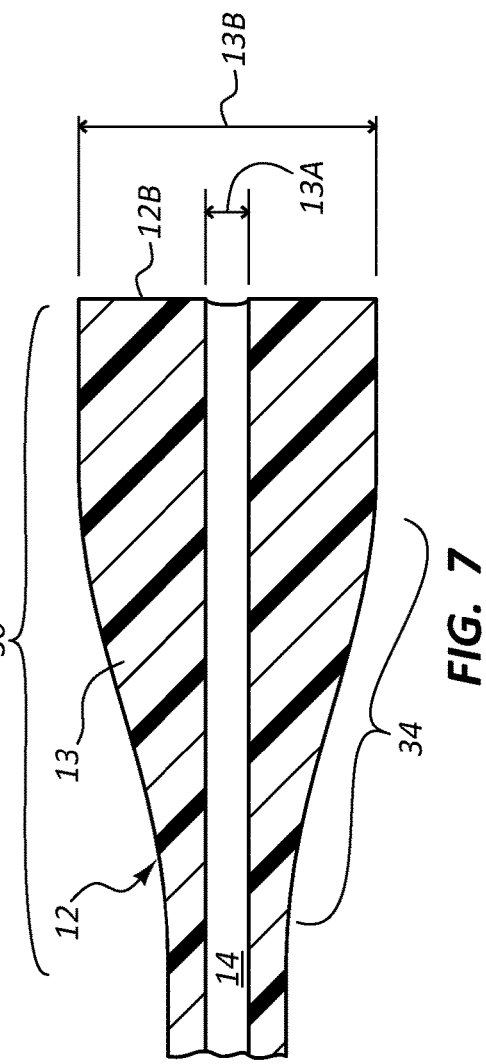
FIG. 7 is a cross sectional view of a distal portion of a catheter tube in accordance with one embodiment.

FIG. 7 shows a single lumen the catheter tube 12 according to one embodiment, wherein the distal portion 30 includes the distal taper portion 34 such that a flared outer diameter 13B is defined by the outer wall 13. An inner diameter 13A defined by the lumen 14 remains substantially constant through the distal portion 30. The resulting increase in thickness of the outer wall provides stability for the distal portion 30 during fluid infusion into the vessel, thus reducing or preventing undesired distal tip whipping.

Figure 8:
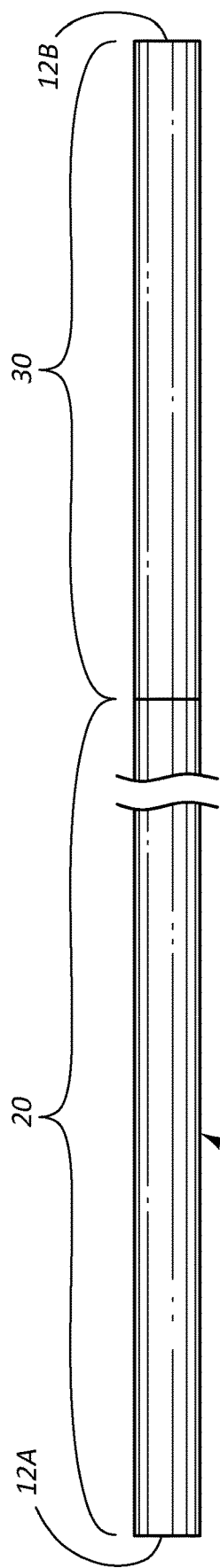
FIG. 8 is a side view of a catheter tube in accordance with one embodiment.

FIG. 8 shows that, in one embodiment, the proximal portion 20 and the distal portion 30 of the catheter tube 12 can be configured so as to exhibit differing levels of the stiffness, or elastic modulus, E (see equation (1)). For instance, in the present embodiment the proximal portion 20 includes a relatively soft material while the distal portion 30 includes a relatively stiffer material so as to provide extra strength at the distal end in order to increase the elastic modulus E of the distal portion, in turn reducing or preventing distal tip whipping. In yet another embodiment, the proximal and distal portions can exhibit similar stiffness at room temperature, but exhibit differing stiffness after implantation and subjection to internal body temperatures.

In one embodiment, both the proximal and distal portions are formed of a similar material, with the distal portion being treated to be stiffer relative the proximal portion. Examples of such treatment of the distal portion include irradiation, application of a solvent or activator, heat treatment, etc. In another embodiment, it is the proximal portion that is treated to exhibit a less-stiff elastic modulus.

In one possible embodiment, the entire length of the catheter tube can be treated so as to exhibit a relatively stiff modulus. In another embodiment, the catheter tube can be extruded from two different materials to provide a soft proximal portion and a relatively stiffer distal portion. In yet another embodiment, a soft proximal tube portion can be formed then joined via adhesion to a pre-formed, relatively stiffer distal portion. These and other variations are therefore contemplated.

Figure 9:
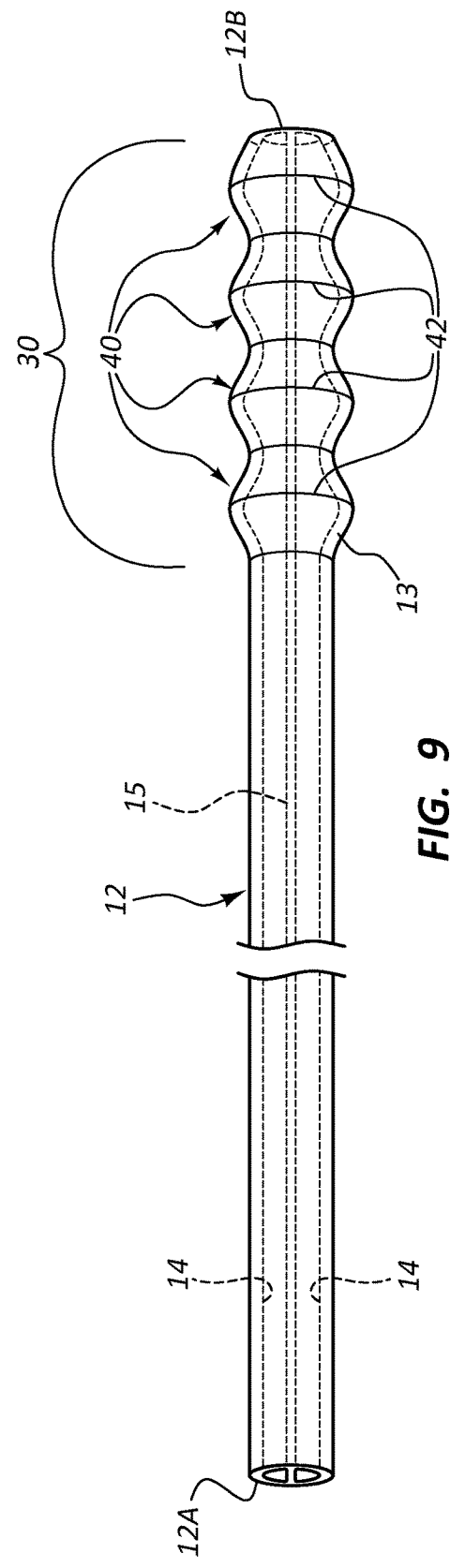
FIG. 9 is a side view of a catheter tube in accordance with one embodiment.

FIG. 9 shows details of the catheter tube 12 according to another embodiment, wherein the distal portion 30 of the tube outer wall 13 defines a plurality of flared segments 40 that each include an annular maximum diameter point 42. The catheter tube 12 here is a dual lumen tube with the lumens 14 separated by the septum 15. The plurality of flared segments gives the catheter tube 12 a knurled appearance. The annular flared segments 40 are configured such that any one of the segments can be cut at about the respective maximum diameter point 42, thus shortening the catheter length and providing relatively large and stable distal end fluid outlets for the lumens 14. Again, because of its flared configuration for each of the catheter tube lumens 14, the distal portion 30 of the catheter tube 12 exhibits relatively larger values for both the areal size A of the lumens and the area moment of inertia I. The number, size, and placement of the flared segments can vary according to application or catheter configuration.

FIG. 10 shows details of the catheter tube 12 according to another embodiment, wherein the tube defines first and second lumens 14A and 14B separated by the septum 15. As shown, the outer wall 13 of the catheter tube 12 remains cylindrical while the septum 15 in the distal portion 30 includes a plurality of wave formations 46 that together define an undulating pattern. The distal portion 30 of the catheter tube 12 here is trimmable such that the lumen size configuration at the trimmed distal tip can be specifically selected. This shown in FIGS. 11A and 11B, wherein if the catheter tube 12 is trimmed at the location indicated at 11A-11A in FIG. 10, the lumen 14A will be larger in area relative to the lumen 14B at the distal tip of the tube (FIG. 11A).

In contrast, trimming the catheter tube 12 at the location indicated at 11B-11B in FIG. 10 will result in the distal tip lumen configuration shown in FIG. 11B, wherein the lumen 14B is larger in area relative to the lumen 14A. In this way, a particular lumen 14 of the catheter tube 12 can be selected to have a relatively larger distal tip opening in order to stabilize the distal portion 30 within the vessel when fluid is infused into the vessel from that lumen. Thus, it is seen that the undulating septum causes the cross sectional sizes of the lumens 14A and 14B to vary inversely with respect to one another as a function of length along the catheter tube 12. Of course, the catheter tube here can also be employed without first being trimmed.

Figure 12:
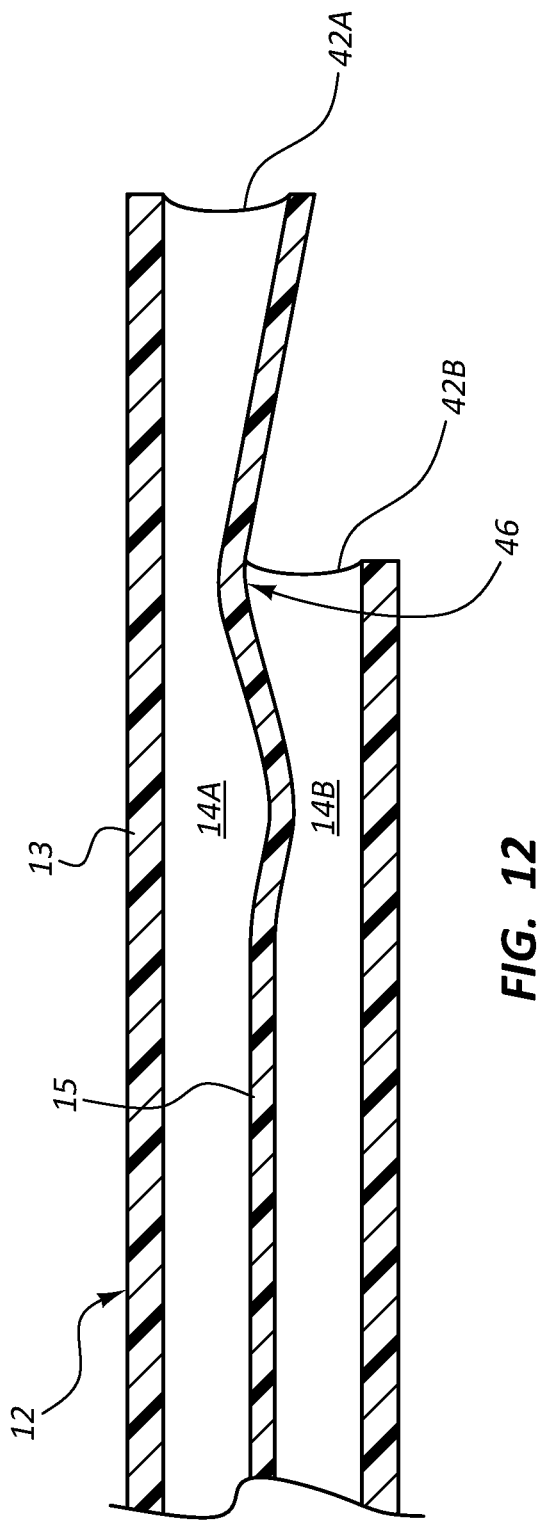
FIG. 12 is a cross sectional side view of a distal portion of a catheter tube in accordance with one embodiment.

FIG. 12 shows another distal tip trimming configuration for the catheter tube of FIG. 10, wherein the tube is trimmed to define a staggered distal tip. Specifically, the distal tip is trimmed with respect to the septum wave formations 46 such that the areal size of the tip opening 42A and 42B for each lumen 14A and 14B, respectively, is maximized. This results in enhanced stability of the distal portion of the catheter tube 12 within the patient's vessel during fluid infusion due to the increase in lumen area A at the catheter tube distal tip. Of course, other staggered tip configurations can be employed.

Figure 13:
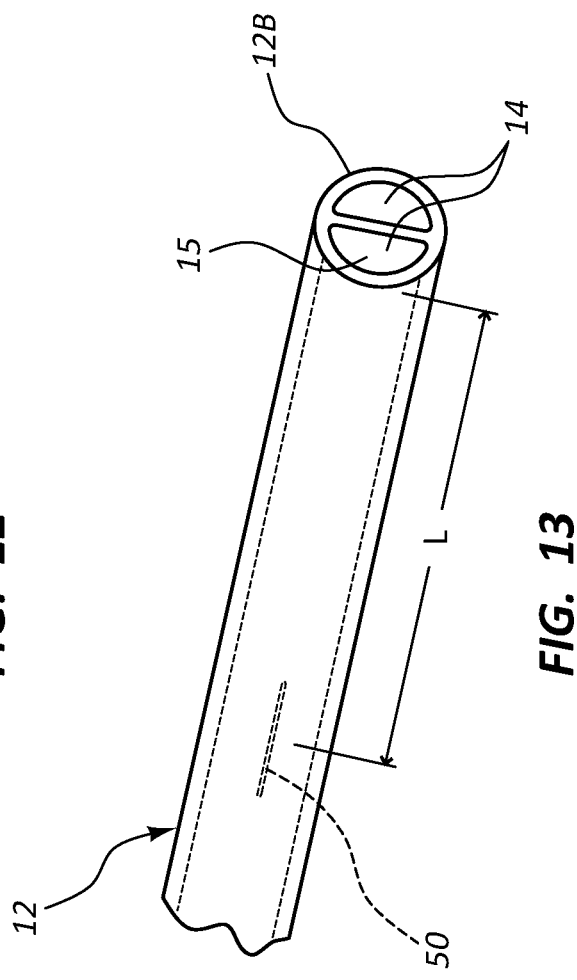
FIG. 13 is a perspective view of a distal portion of a catheter tube in accordance with one embodiment.

FIG. 13 shows details of a dual lumen catheter tube 12 according to another embodiment, wherein the dual lumens 14 of the tube are separated by the septum 15. At a predetermined distance L from the distal end 12B of the catheter tube 12, a slit 50 is defined in the septum 15 such that fluid communication is established between the lumens 14. So configured, the slit 50 enables the passage of fluid from one lumen 14 to the other lumen during fluid infusion into the vessel of the patient in which the catheter tube 12 is disposed. This in turn lowers the fluid pressure in the lumen 14 from which fluid is passing through the slit 50 and increases usable lumen area through which the fluid may pass from the catheter tube 12 into the vessel. These effects contribute to increase tip stability and to prevent distal tip whipping within the vessel. Note that the size, shape, number, positioning, and other variations of the slit can change according to other embodiments.

Figure 14A:
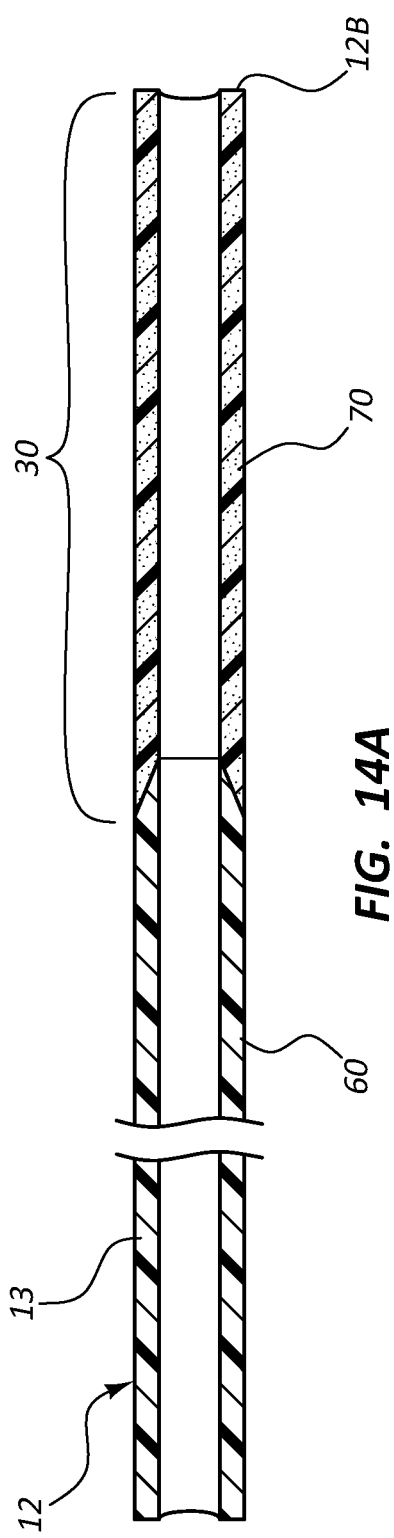
FIGS. 14A and 14B are cross sectional side views of a catheter tube in accordance with one embodiment.
Figure 14B:
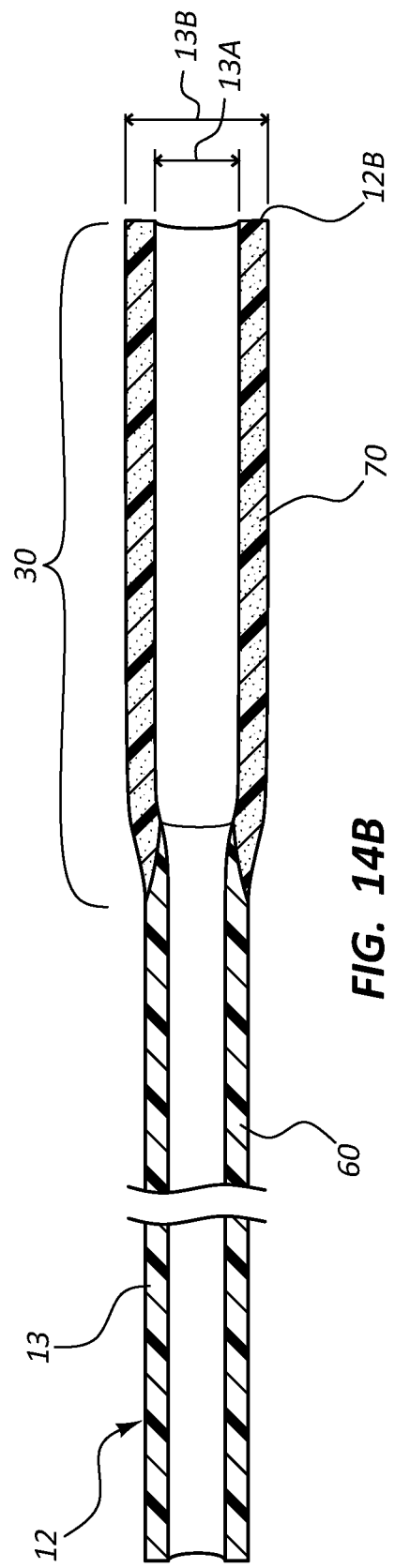

FIGS. 14A and 14B show details of the catheter tube 12 according to another embodiment, wherein a proximal portion of the catheter tube outer wall 13 includes a non-swellable first material 60. The distal portion 30 of the outer wall 13 includes a second material 70 that is configured to define a similar form factor to the proximal portions of the catheter tube including the first material 60 before insertion into the patient's body. In contrast to the first material 60, however, the second material 70 is configured to swell to a larger size when subjected to body heat or moisture after insertion into the vasculature of the patient.

So configured, the distal portion 30 of the catheter tube 12 initially defines a similar outer diameter as that of the more proximal tube portion (FIG. 14A), thus facilitating relative ease in inserting the catheter tube into the patient vasculature. After placement is complete, the second material 70 of the distal portion 30 swells (FIG. 14B) to a larger inner diameter 13A and outer diameter 13B relative to the more proximal catheter tube portion so as to provide a larger lumen area and outer wall thickness, which cooperate to increase distal tip stability. One example of a swellable material for use as the second material 70 is a biomaterial including polyurethane and polyethylene oxide sold under the trademark AQUAVENE of Pierre Fabre Dermo-Cosmetique. Other swelling materials, such as suitable hydratable and hydrophilic materials can also be employed. Use of a swelling material therefore serves as another example, in addition to the other embodiments described herein, for providing a catheter tube with a stable distal portion.

FIGS. 15 and 16 depict other configurations for use of the swellable material 70 described above in connection with FIGS. 14A and 14B. In particular, FIG. 15 shows inclusion of the swellable second material 70 in the catheter tube 12 to define only an external tubular portion of the distal portion 30 of the catheter tube 12. The internal tubular portion of the distal portion 30, as well as the more proximal portions of the catheter tube 12, is defined by the non-swelling first material 60.

In FIG. 16, the swellable second material 70 extends proximally beyond the distal portion 30 into more proximal portions of the catheter tube 12 to define at least a portion of the outer surface of the catheter tube. A catheter tube manufactured in this fashion can be designed so as to vary in a predetermined and controlled manner the degree of swelling of the catheter tube along the length thereof after insertion into the patient by controlling the amount of swellable material included in the outer wall along the tube length. It is noted that where a hydrophilic material is included in the swellable material and defines the catheter tube in a manner similar to that shown in FIG. 16, the hydrophilic material can improve the biocompatibility of the catheter tube in certain circumstances. Further note that the embodiments of FIGS. 15 and 16 isolate the swellable material 70 from direct contact with fluids passing through the lumen of the catheter tube for infusion into the patient, thus preventing unintended absorption of the fluids by the swellable material. It is appreciated that the above catheter tube configurations can be formed via extrusion or other suitable method. Also note that these configurations are just examples of many possible catheter tube designs including swellable and non-swellable materials.

Note that though the distal portions of the catheter tubes described above include both increased outer wall thickness and increased lumen area relative to the more proximal portions of the catheter tubes, in other embodiments the outer wall thickness can vary independently of lumen area in the distal portion, and vice versa. Further, the length and relative size of the distal, proximal, and portions of the catheter tube can also vary from what is shown and described herein. Note also that various single and dual lumen catheters are described herein, but other multi-lumen catheters and tubular indwelling medical devices can also benefit from the teachings herein.

Figure 17:
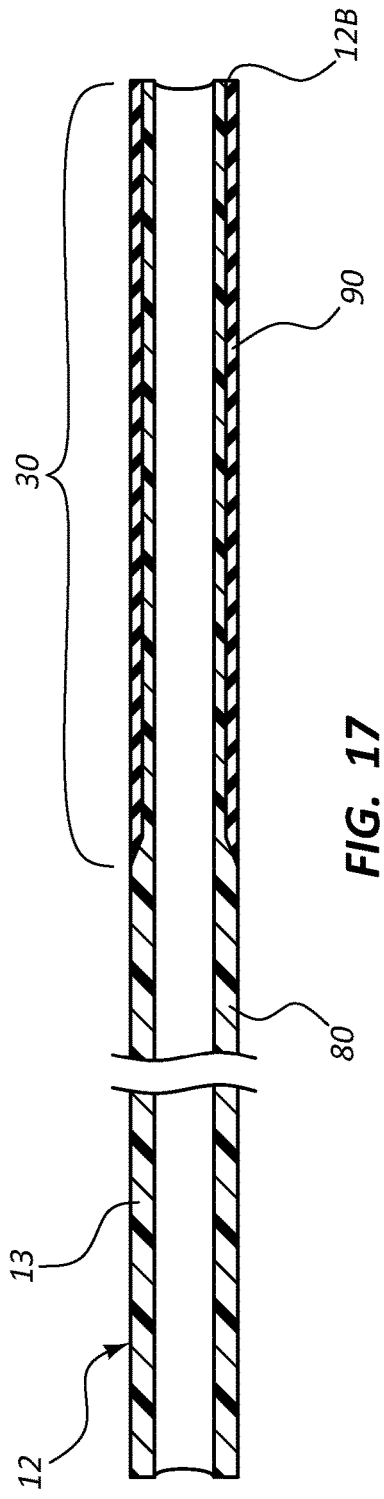
FIG. 17 is a cross sectional side view of a catheter tube in accordance with one embodiment.
Figure 18:
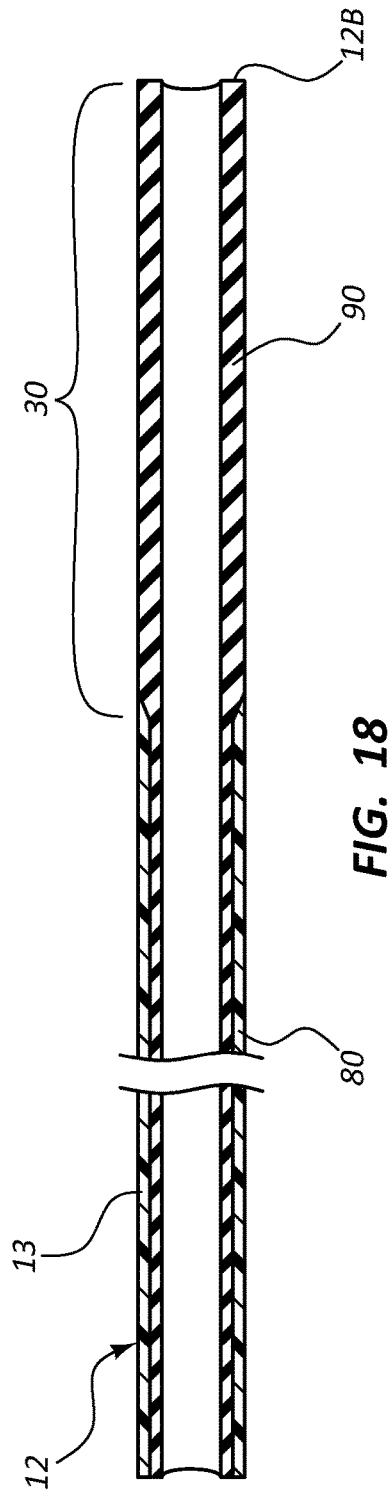
FIG. 18 is a cross sectional side view of a catheter tube in accordance with one embodiment.
Figure 19:
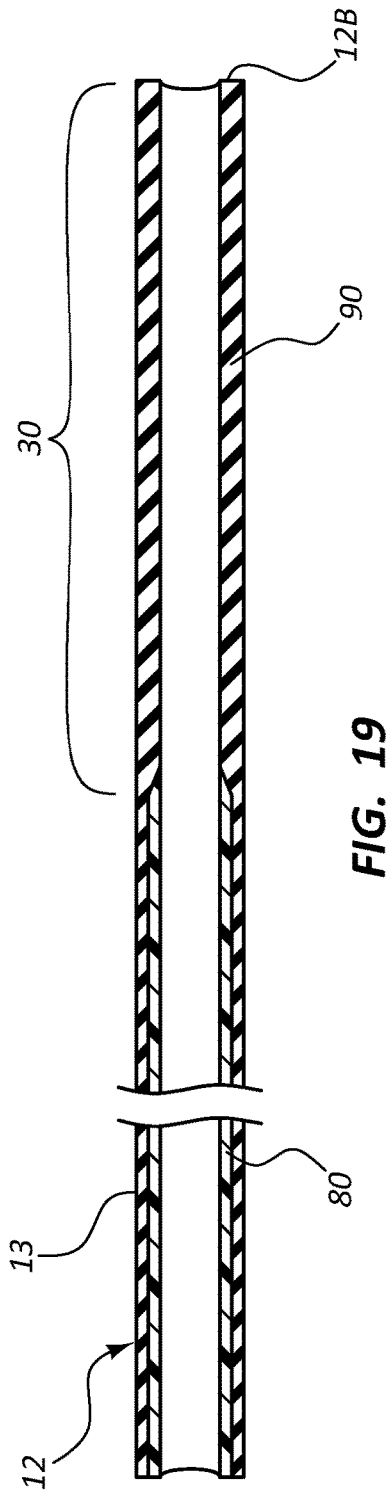
FIG. 19 is a cross sectional side view of a catheter tube in accordance with one embodiment.

FIGS. 17-19 show details of the catheter tube 12 according to possible embodiments, wherein the catheter tube includes a multi-durometer configuration. In particular, FIG. 17 shows the catheter tube 12 formed by the outer wall 13, a proximal portion of which includes a relatively hard (high durometer) first material 80. The first material 80 extends distally to the distal end 12B of the catheter tube 12 to define an inner diameter in the distal portion 30 of the tube. A second material 90 that is softer (low durometer) relative the first material 80 is included atop the first material in the distal portion 30 to define an outer diameter surface of the distal portion. Such a multi-durometer construction can be achieved via a selective extrusion/coextrusion process, extrusion of the first material 80 followed by coating or other application of the second material 90, etc. These and other manufacturing methods are contemplated for this and the other embodiments depicted in the succeeding figures.

The design of the catheter tube 12 as shown in FIG. 17 enables the distal portion 30, which is inserted into the patient's vasculature, to be relatively soft so as to enable the catheter tube to bend and be readily positioned within a vessel without causing trauma to the vessel. In contrast, the more proximal portion of the catheter tube 12 formed from the first material 80 remains external to the patient in the present embodiment and is relatively harder with respect the second material 90 so as to enable it to withstand the relatively higher fluid pressures present in the proximal portion of the catheter tube when fluid is infused therethrough.

FIG. 18 shows another possible catheter tube embodiment, wherein the distal portion of the catheter tube 12 is formed exclusively from the relatively soft second material 90. The second material 90 also extends proximally from the distal portion 30 of the catheter tube 12 to define an inner diameter of the more proximal portions of the tube, while the relatively harder first material 80 extends proximally from the distal portion 30 to define an outer surface of the catheter tube, as shown. Such a configuration increases the softness and flexibility of the catheter tube 12 along its entire length, with substantial softness along its distal portion 30.

In FIG. 19, another possible catheter tube embodiment is shown, wherein the distal portion of the catheter tube 12 is again formed exclusively from the relatively soft second material 90. The second material 90 also extends proximally from the distal portion 30 of the catheter tube 12 to define an outer surface of the more proximal portion of the tube, while the relatively harder first material 80 extends proximally from the distal portion 30 to define an inner diameter of the catheter tube, as shown. As with the previous two embodiments, such a configuration increases the softness and flexibility of the catheter tube 12 along its entire length, with substantial softness along its distal portion 30.

FIGS. 20 and 21 show that, in other embodiments, the multi-durometer catheter tube can also vary in diameter. For instance, FIG. 20 shows the distal portion 30 of the catheter tube 12 as including an outer portion of the outer wall 13 formed by the second material 90 and the inner diameter 13A defined by the first material 80. The first material 80 extends proximally from the distal portion 30 to define the more proximal portion of the tube outer wall 13, thus defining the uniformly sized inner diameter 13A along the entire length of the catheter tube 12. The more proximal portion of the catheter tube 12 defined by the first material 80 is also sized to a larger diameter than the distal portion 30. FIG. 21 shows a similar configuration as that of FIG. 20, with the first material 80 defining a varying inner diameter for the catheter tube 12. Thus, these embodiments illustrate the many variations possible with multi-durometer catheter tube combinations. It should be appreciated that various other configurations are possible, including reverse configurations of those illustrated and described herein. Non-limiting examples of materials that may be employed include the thermoplastics mentioned further above including an 80-95A durometer range for the second material 90, and a 95A-60D durometer range for the first material 80.

Figure 23A:
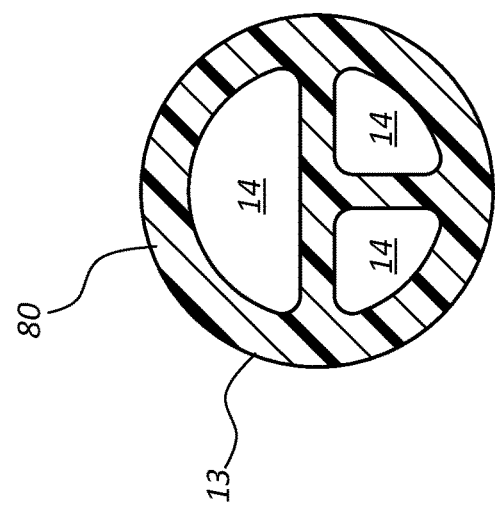
FIGS. 23A-23C are cross sectional views of the catheter tube of FIG. 22.
Figure 23B:
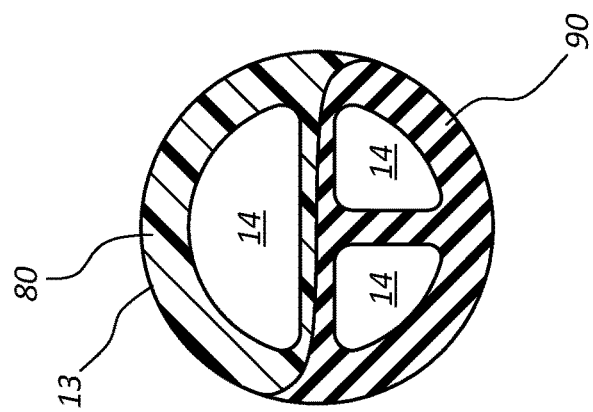
Figure 23C:
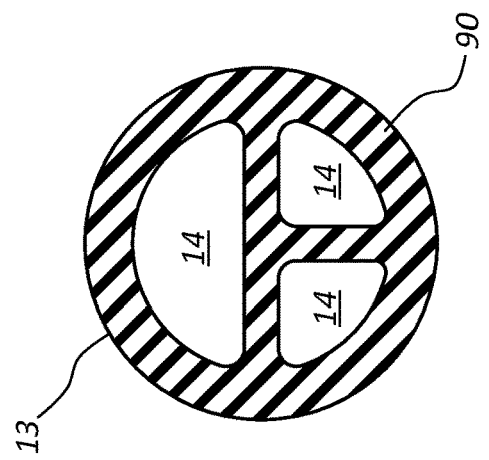

FIG. 22 shows another multi-durometer catheter tube 12 according to one embodiment, including the outer wall 13 defined by both the relatively hard first material 80 and the relatively soft second material 90. As shown, the proximal end 12A of the catheter tube 12 is defined completely by the first material 80, which tapers down gradually in the distal direction so as to define an increasingly smaller portion of the outer wall 13 (and septum, if present). Correspondingly, the second material 90 defines a small portion of the catheter tube 12 proximate the proximal end 12A and tapers up gradually in the distal direction so as to define an increasingly greater portion of the outer wall 13 (and septum, if present) until at the distal end 12B the entirety of the catheter tube is defined entirely by the second material 90. This varying definition of the catheter tube outer wall can be seen in the cross sectional views of FIGS. 23A-23C, which are views at the corresponding indicated locations along the catheter tube shown in FIG. 22. Thus, each point along the length of the catheter tube 12 include a unique proportion of contribution to the outer wall composition by the first material 80 and the second material 90. Such a catheter tube as shown at 12 here can be manufactured using a co-extrusion or other suitable process.

Definition of the catheter tube 12 in the manner shown in FIG. 22 enables the distal portion of the tube to be substantially softer relative more proximal portions of the tube, which is useful for providing less traumatic insertion of the tube into the vessel of the patient while still providing a relatively hard proximal portion for withstanding the relatively greater pressures present in the proximal tube portion during power injection or other fluid infusion procedures. It is appreciated that variations to this design can be employed, including the contribution to the outer wall composition being varied in a step-wise fashion as opposed to the continuous fashion shown in FIG. 22, reversal of the first and second materials, etc.

Figure 24:
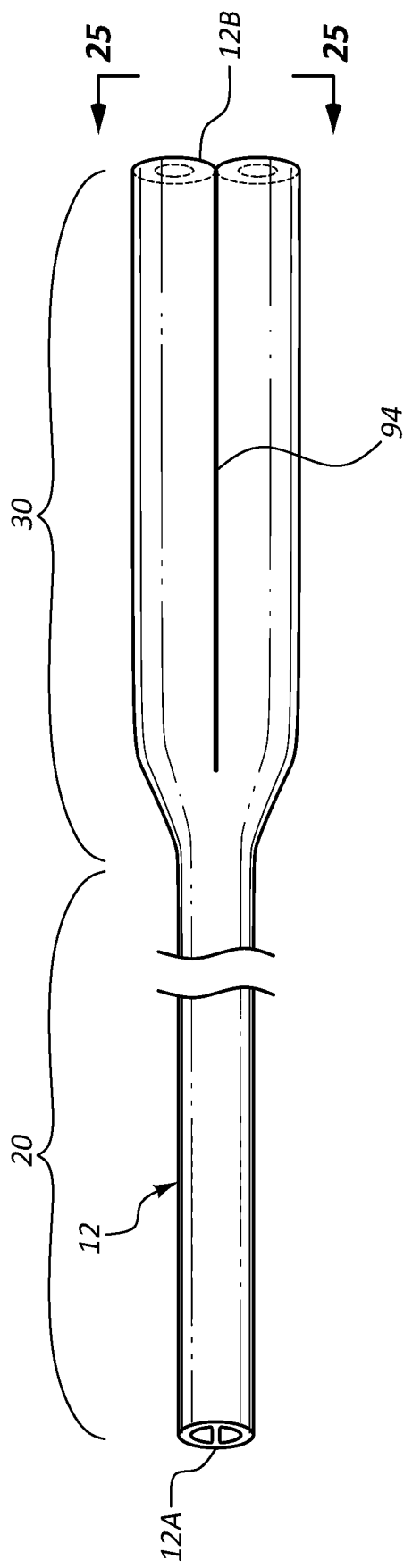
FIG. 24 is a side view of a catheter tube in accordance with one embodiment.
Figure 25:
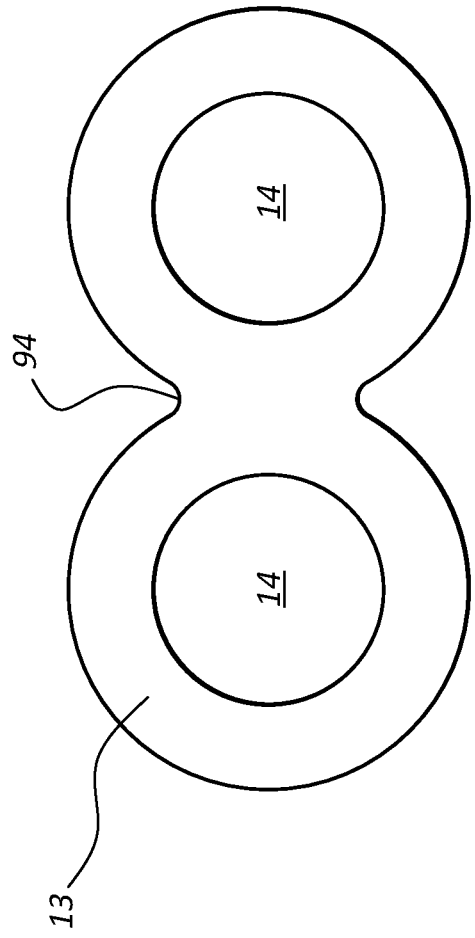
FIG. 25 is a distal end view of the catheter tube of FIG. 24.

FIG. 24 gives various details of another configuration of the catheter tube 12 according to one embodiment, wherein the tube is dual lumen and the distal portion 30 is flared to define a diameter greater relative to that of the proximal portion 20. The tube 12 in the distal portion 30 includes two single lumen tube structures, each defining one of the lumens 14, which are joined via a crease 94 therebetween, best seen in FIG. 25. This configuration offers the same benefits of a flared distal portion as in previous embodiments, e.g., reduction in distal tip whipping within the vessel.

Figure 27:
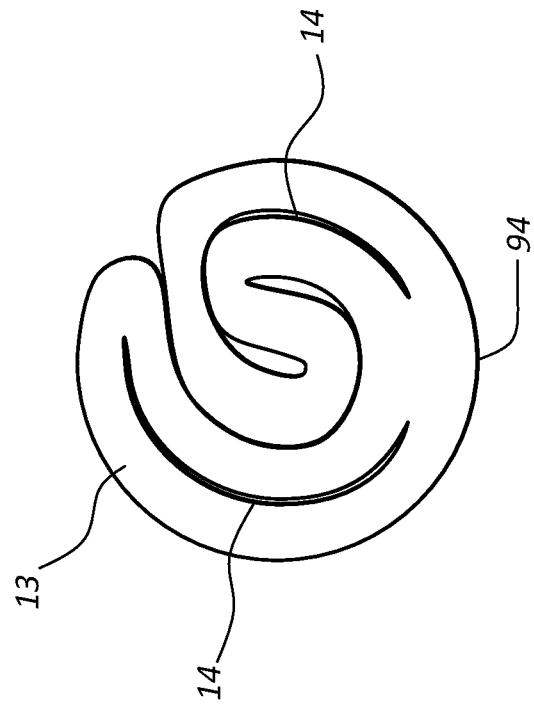
FIG. 27 is a distal end view of the catheter tube of FIG. 24 in a second rolled-up configuration.
Figure 26:
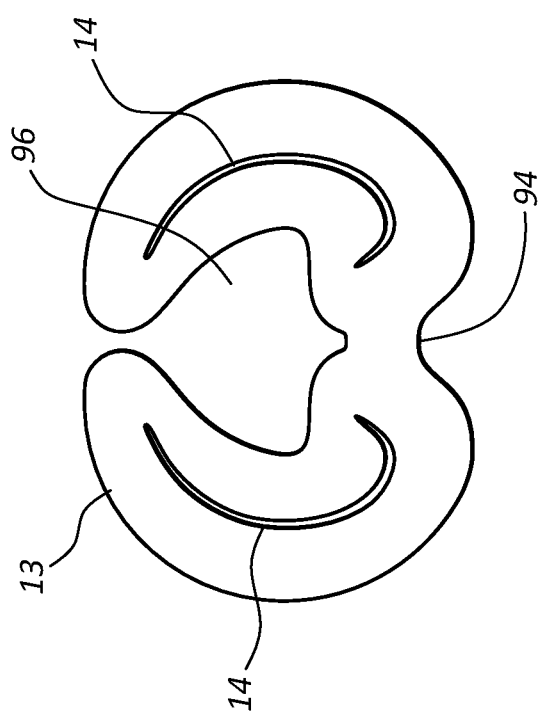
FIG. 26 is a distal end view of the catheter tube of FIG. 24 in a first rolled-up configuration.

FIGS. 26 and 27 show that the outer wall 13 that defines the distal portion 30 of the catheter tube 12 can be folded or compressed in order to substantially match in diameter the diameter of the proximal portion 20. This enables the catheter tube 12 to be fed through an introducer and into the patient vessel. After placement of the catheter tube 12 within the vessel is complete, the distal portion can unfold to its full size shown in FIG. 25.

For instance, FIG. 26 shows that the outer wall 13 defining the distal portion 30 of the catheter tube 12 can be compressed so as to close the lumens 14 and define a substantially closed, longitudinally extending cavity 96. The cavity 96 is suitable in one embodiment for receiving therethrough a guidewire for guiding the catheter tube into the vessel. A dissolvable adhesive or other suitable substance can be applied to the catheter tube outer wall 13 so as to maintain the tube in the compressed state until placement within the patient's vasculature is complete. The adhesive can then dissolve, enabling the distal portion 30 of the catheter tube 12 to expand to its fully open state.

FIG. 27 shows the outer wall 13 in a rolled configuration that enables the distal portion 30 of the catheter tube 12 to assume a diameter substantially similar to that of the proximal portion 20 so as to ease catheter tube insertion into the patient's vasculature. Again, a dissolvable adhesive or other suitable substance can be employed to maintain the distal portion outer wall 13 in the rolled configuration during insertion. In addition to the configurations shown in FIGS. 26 and 27, other compression configurations are also possible. Also, catheter tubes defining more or fewer than two lumens can also benefit from the principles described herein. In the illustrated and other embodiments described herein, it is further appreciated that the cross sectional geometry can also vary from proximal to distal ends, such as from round to oval, in one non-limiting example.

Figure 28B:
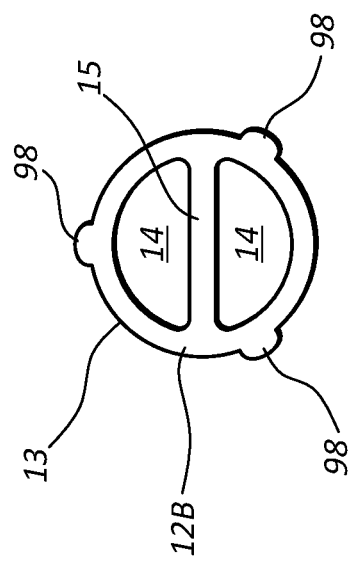
FIGS. 28A and 28B are perspective and end views, respectively, of a catheter tube in accordance with one embodiment.
Figure 28A:
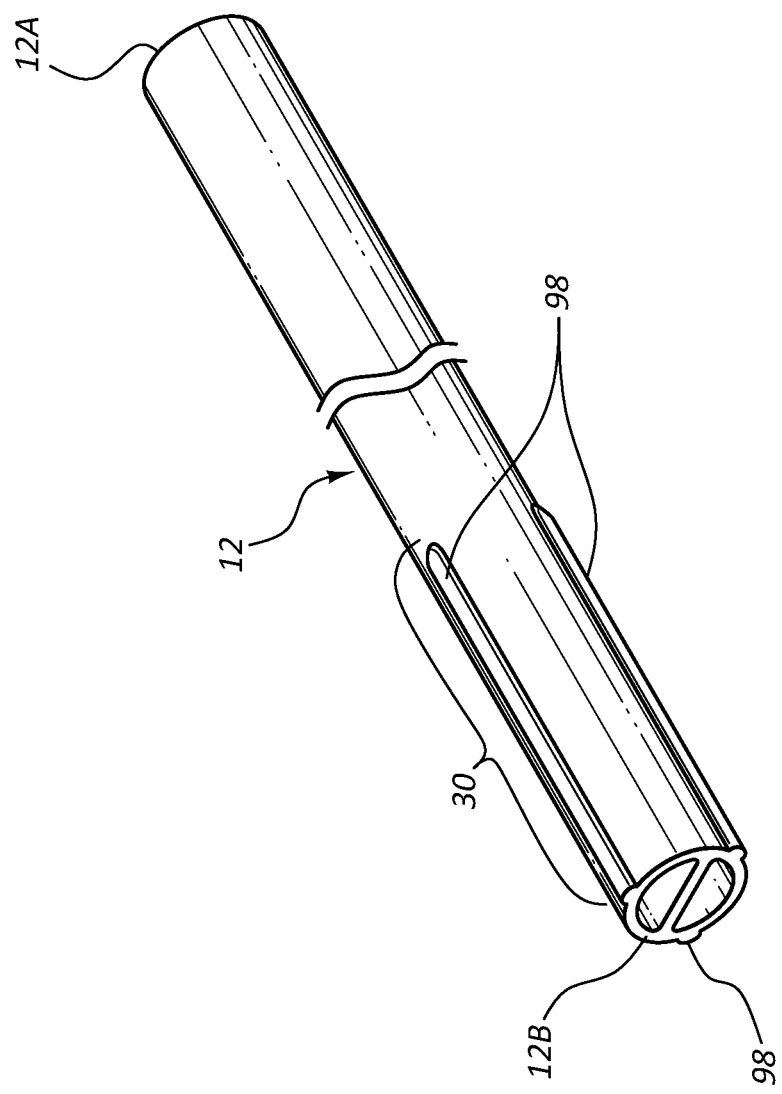

FIGS. 28A and 28B depict yet another stable configuration for the distal portion 30 of the catheter tube 12, wherein a plurality of longitudinally extending stiffening ribs 98 are disposed on the outer wall 13. The ribs 98 serve to increase the area moment of inertia I for the catheter tube distal portion 30, thus increasing tube stability during fluid infusion therethrough and reducing or preventing distal tip whipping. Though three ribs are shown disposed about the circumference of the catheter tube 12, more or fewer than this can be employed. Also, the size, shape, length, and placement of the ribs can vary from what is shown in FIGS. 28A and 28B. In one embodiment, the ribs can be disposed on an inner lumen surface of the distal portion.

In addition to the catheter tubes described herein as part of catheter assemblies, the principles disclosed can be employed with other tubular medical devices as well.

Figure 29:
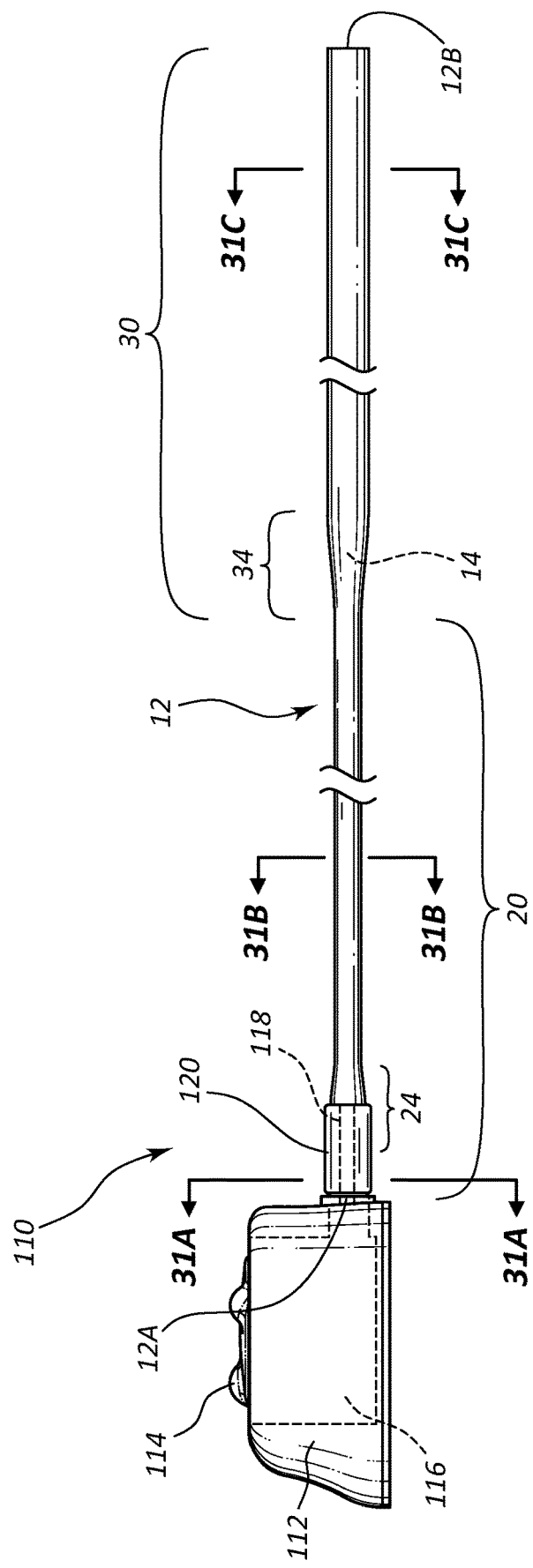
FIG. 29 is a side view of a vascular access port system according to one embodiment.

Reference is now made to FIG. 29, which depicts various details of an access port assembly 110 according to one embodiment, including an implantable vascular access port ("access port") 112 and a catheter tube, such as the catheter tube 12, operably connected to the access port.

In greater detail, the access port 112 includes a body that defines a reservoir 116 to which is access is provided via a needle-penetrable septum 114 covering an opening to the reservoir. A stem 118 provides an outlet to the reservoir 116 and is configured to operably connect with the catheter tube 12 via a locking component 120. In one embodiment, the locking component 120 includes a Cath-Lock-type catheter locking component available from Bard Access Systems, Salt Lake City, Utah. In the present embodiment, the access port 112 (and the catheter tube 12) is configured for power injection of fluids therethrough, where the fluid flow rate is about 5 cc or more per second. In other embodiments, the access port and/or catheter tube need not be power injectable.

As shown in FIG. 29, the catheter tube 12 is configured similar to that shown in FIG. 2-3C, including the lumen 14 extending between the proximal end 12A and the distal end 12B of the catheter tube and defining the proximal portion 20 and the distal portion 30. As before, the proximal taper region 24 is disposed adjacent the catheter tube proximal end 12A and provides a transition in cross sectional area of the lumen 14 from a predetermined cross sectional lumen area at the catheter tube proximal end 12A to a relatively smaller cross-sectional lumen area distal to the proximal taper region 24 of the proximal portion 20, as shown in FIGS. 31A and 31B, which cross sectionally depict the outer wall 13 of the catheter tube 12 and the lumen 14 it bounds at the indicated points (in FIG. 29) along the longitudinal length of the catheter tube. Note that the catheter tube 12 defines at least one lumen; as such, the catheter tube can include a single lumen as in the present embodiment, or more lumens as may be needed.

Figure 30:
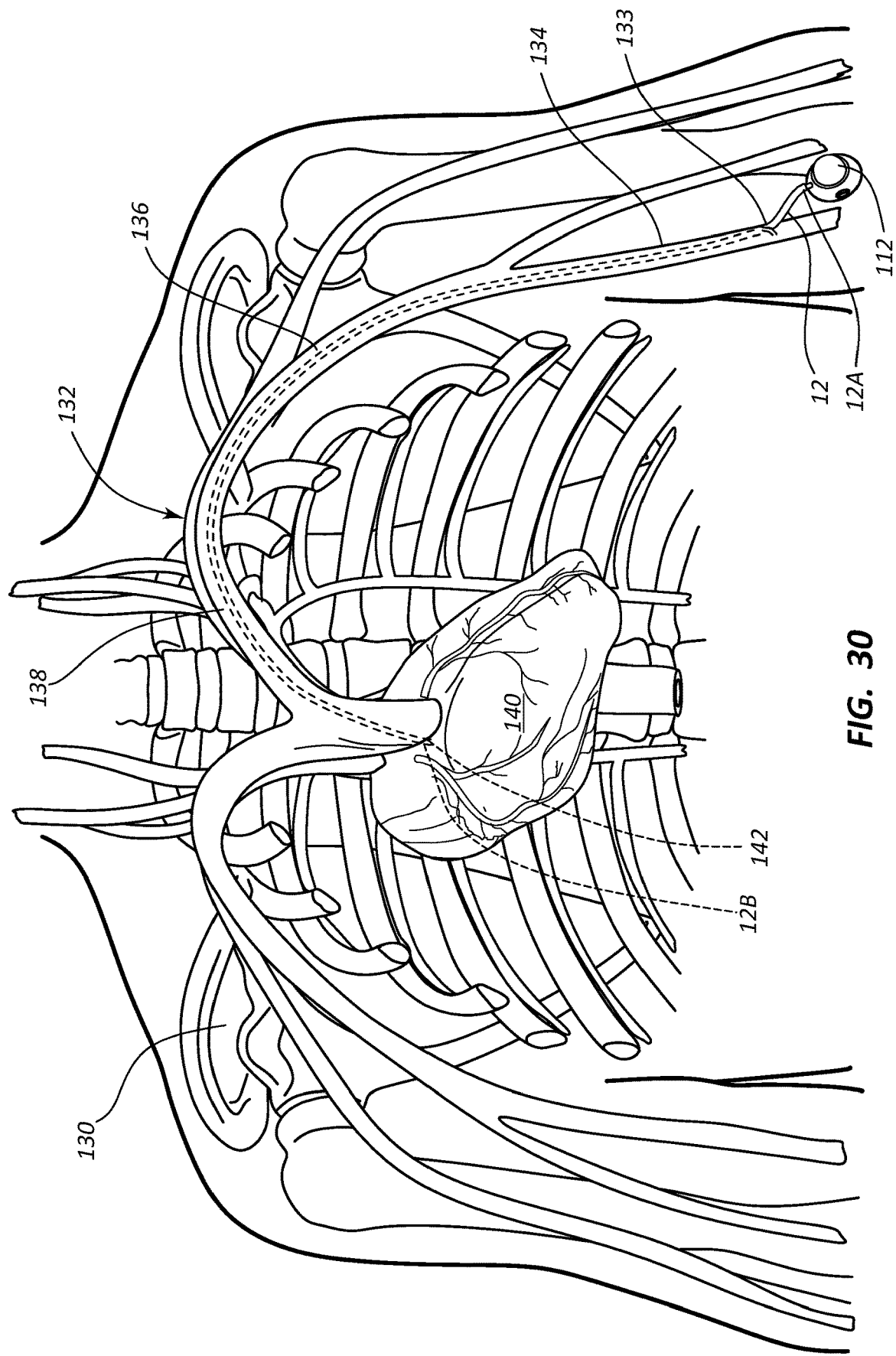
FIG. 30 is a simplified cutaway view of a patient with the vascular access port system of FIG. 29 disposed therein, according to one embodiment.

Note that an inner diameter of the stem 118 of the access port 112 in the present embodiment is larger relative to other access ports of similar size so as to match the relatively large cross sectional area of the lumen 14 in the proximal taper region 24 of the catheter tube 12 when the stem and catheter tube are operably attached in a fluid-tight configuration. So configured, a relatively higher fluid flow rate through the stem 118 and catheter tube 12 is possible. As seen in FIG. 30, this proximal taper region 24 of the catheter tube 12 is not typically disposed in the vein, but rather resides outside thereof; thus, the relatively larger size of the stem 118 and the proximal taper region does not impact occlusion of the vein in which more distal parts of the catheter tube are disposed.

Figure 31C:
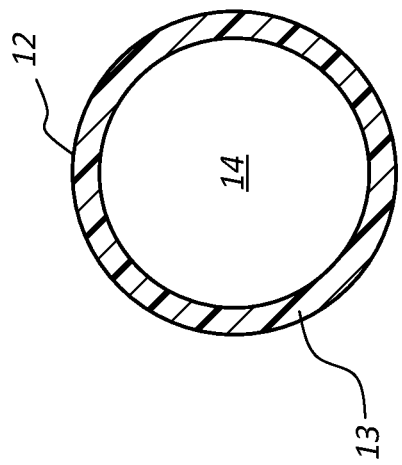
FIGS. 31A-31C are cross sectional views of the catheter tube of FIG. 29, showing a relative change in catheter tube structure.
Figure 31B:
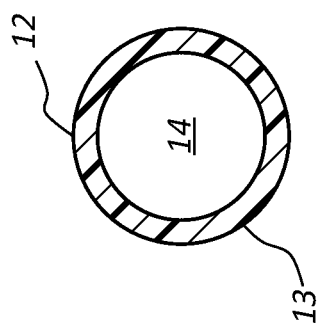
Figure 31A:
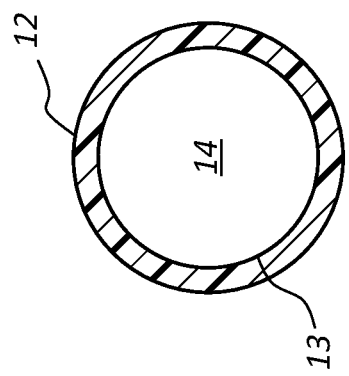

Similarly, the distal portion 30 includes the distal taper region 34, disposed at the proximal end of the distal portion adjacent to the distal end of the proximal portion 20, which provides a transition in cross sectional area of the lumen 14 from a predetermined cross-sectional lumen area proximal to the distal taper region 34 to a relatively larger cross-sectional lumen area distal to the distal taper region and extending to the catheter tube distal end 12B, as shown in FIGS. 31B and 31C. Note that, though the cross sectional lumen area of the distal portion 30 in the present embodiment remains constant distal to the distal taper region 34, in other embodiments the cross sectional area of the distal portion could increase continuously (or in some other fashion) toward the distal end 12B of the catheter tube 12.

The particular function and aspects of the catheter tube 12 of FIG. 29 as described here are similar to those discussed further above in connection with FIGS. 1-3C. In the illustrated embodiment, the non-tapered segment of the proximal portion 20 of the catheter tube 12 is sized as a 5 French catheter portion while the non-tapered segment of the distal portion 30 is sized as a 6 French catheter portion. In yet another embodiment, the non-tapered segment of the proximal portion 20 of the catheter tube 12 is sized as a 4 French catheter portion. In yet another embodiment, the non-tapered segment of the distal portion 30 of the catheter tube 12 is sized as an 8 French catheter portion. This notwithstanding, other sizes and relative size differences between the proximal and distal catheter tube portions, both smaller and larger, are also possible.

Reference is now also made to FIG. 30, which depicts disposal of the access port assembly 110 within a patient 130, according to one embodiment. As shown, the access port 112 is disposed in a subcutaneous pocket defined in an upper arm portion of the patient 130, though many other placement locations, including other limbs, are possible for the access port. The proximal end 12A of the catheter tube 12 is operably attached to the stem 118 of the access port 112, and that catheter tube extends into a vasculature 132 of the patient via an incision 133 defined in a vessel proximate the subcutaneous pocket in which the access port 112 is disposed. Note that placement of the access port 112 in an arm of the patient is often preferred so as to better obscure the presence of the port and to avoid the creation of a scar on the patient's chest, as occurs when the port is placed in the chest of the patient. Note, however, that the principles to be described below apply to access port assembly placement in the arm, chest, and other body locations.

As shown, the catheter tube 12 extends from the access port 112 and enters a vessel of the patient vasculature 132, such as a basilic vein 134 as depicted in FIG. 30, and extends distally through an axillary vein 136, in the present embodiment. So positioned, the relatively smaller proximal portion 20 of the catheter tube 12 is primarily disposed within the basilic and axillary veins 134, 136, which are relatively small veins, in terms of cross sectional area, given their distance from a heart 140 of the patient 130.

The catheter tube 12 further extends within the patient vasculature 132 such that the distal portion 30 thereof is disposed within a relatively large vein, such as a subclavian vein 138 in the present embodiment. The distal end 12B of the catheter tube 12 terminates at a desired location, such as proximate a superior vena cava ("SVC") 142 of the heart 140 in the present embodiment, as shown in FIG. 30. So positioned, the relatively larger distal portion 30 of the catheter tube 12 is primarily disposed within the subclavian vein 138, which is a relatively large vein in terms of cross sectional area, given its relatively short distance from the heart 140.

In light of the above, it is seen that the relatively small proximal portion 20 of the catheter tube 12 is disposed within the relatively small basilic and axillary veins 134, 136, while the relatively larger distal portion 30 of the catheter tube is disposed within the relatively larger subclavian vein 138. As has been described further above in connection with previous embodiments, this provides several benefits. For one, it helps prevent undesired catheter tube-caused occlusion of the vein by matching the cross-sectional size of the portion of the catheter tube 12 with a corresponding relative cross-sectional size of the vein in which the catheter tube portion is disposed. Also, it assists in reducing the risk of thrombus and intimal damage within the vein. Further, the relatively smaller size of the catheter proximal portion 20 enables it to bend more easily during insertion into the patient's vasculature along a potentially tortuous path, resulting in less trauma and damage to the vessel.

Additionally, the relatively larger size of the distal portion 30 of the catheter tube 12 helps to provide stability to the distal end 12B of the catheter tube when fluids are power injected therethrough, thus helping to prevent whipping of the catheter tube distal end against vessel walls. Because of the relatively larger sizes of the lumen(s) 14 in the proximal taper region 24 and the distal portion 30, fluid flow resistance through the catheter tube 12 is reduced, which is beneficial especially during power injection of contrast media through the catheter tube. In one embodiment, power injection through the catheter tube 12 can exceed typical rates of about 5 cc/second given the relative general increase in catheter tube lumen size, all while preserving a relatively small size for the portion of the catheter tube that resides within relatively small veins, as shown in FIG. 30. Reference is made to Bernoulli's fluid flow principles and general thrust principles, which teach that fluid exiting the distal end 12B of the catheter tube 12 described in connection with FIGS. 29-31C will slow in velocity as it exits and will reduce the thrust force on the catheter tube itself, thus helping to prevent whipping of the distal catheter tube end.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A medical method, comprising:
   implanting a vascular access port;
   inserting a catheter into a blood vessel, the catheter comprising:
   at least one lumen extending from a proximal end to a distal end;
   a proximal portion including a first cross sectional lumen area;
   a distal portion including a second cross sectional lumen area larger than the first cross sectional lumen area, the distal portion designed to prevent whipping when the catheter is disposed in a patient and a fluid exits the at least one lumen; and
   a taper region interposed between the proximal portion and the distal portion, the taper region having a third cross sectional lumen area transitioning from the first cross sectional lumen area to the second cross sectional lumen area; and
   coupling the catheter to the vascular access port.

2. The medical method according to claim 1, wherein the implanting step comprises creating a subcutaneous pocket defined in an upper arm portion of the patient, and inserting the vascular access port into the subcutaneous pocket.

3. The medical method according to claim 2, wherein the inserting step comprises creating an incision in a vein of the patient proximate the subcutaneous pocket, and extending the distal portion of the catheter through the incision and into the vein.

4. The medical method according to claim 3, wherein the inserting step further comprises extending the distal portion of the catheter into a subclavian vein of the patient so that a distal end of the catheter is positioned proximate a superior vena cava of the patient.

5. The medical method according to claim 1, wherein coupling the catheter to the vascular access port comprises sliding a proximal end of the proximal portion of the catheter over a stem of the vascular access port, and securing the proximal end to the stem.

6. The medical method according to claim 1, further comprising power injecting the fluid through the vascular access port and the catheter.

7. The medical method according to claim 1, wherein the distal portion of the catheter includes an area moment of inertia greater than an area moment of inertia of the proximal portion of the catheter.

8. The medical method according to claim 7, wherein at least part of the distal portion of the catheter includes an arithmetic product of an elastic modulus greater than an arithmetic product of an elastic modulus of at least part of the proximal portion of the catheter.

9. The medical method according to claim 1, wherein the proximal portion of the catheter includes a proximal taper region transitioning from a fourth cross sectional lumen area at a proximal end of the catheter to the first cross sectional lumen area, the fourth cross sectional lumen area greater than the first cross sectional lumen area.

* * * * *